United States Patent
Macri et al.

(10) Patent No.: US 11,682,480 B2
(45) Date of Patent: *Jun. 20, 2023

(54) SYSTEM AND METHOD FOR PRE-ACTION TRAINING AND CONTROL

(71) Applicants: Vincent J. Macri, Tallahassee, FL (US); Vincent James Macri, New York, NY (US); Paul Zilber, Plainview, NY (US)

(72) Inventors: Vincent J. Macri, Tallahassee, FL (US); Vincent James Macri, New York, NY (US); Paul Zilber, Plainview, NY (US)

( * ) Notice: Subject to any disclaimer, the term of this patent is extended or adjusted under 35 U.S.C. 154(b) by 83 days.

This patent is subject to a terminal disclaimer.

(21) Appl. No.: 17/201,246

(22) Filed: Mar. 15, 2021

(65) Prior Publication Data

US 2021/0202068 A1    Jul. 1, 2021

Related U.S. Application Data

(63) Continuation of application No. 16/834,614, filed on Mar. 30, 2020, now Pat. No. 10,950,336, which is a
(Continued)

(51) Int. Cl.
*G16H 20/70* (2018.01)
*G16H 20/30* (2018.01)
(Continued)

(52) U.S. Cl.
CPC ......... *G16H 20/70* (2018.01); *A63B 24/0075* (2013.01); *G09B 19/003* (2013.01); *G16H 20/30* (2018.01)

(58) Field of Classification Search
CPC .................................................. A63B 24/0075
(Continued)

(56) References Cited

U.S. PATENT DOCUMENTS 5,078,152 A    1/1992    Bond et al.
5,429,140 A    7/1995    Burdea et al.
(Continued)

FOREIGN PATENT DOCUMENTS

JP    2002306632 A    10/2002
KR    20120137327 A    12/2012
(Continued)

OTHER PUBLICATIONS

Kynan Eng et al., "Interactive visuo-motor therapy system for stroke rehabilitation," Medical & biological engineering & computing, vol. 45, No. 9, 2007, pp. 901-907.
(Continued)

*Primary Examiner* — Thomas J Hong
(74) *Attorney, Agent, or Firm* — Resolute Legal PLLC

(57) ABSTRACT

A system for improving physical motor control of affected human extremities and related cognitive and nervous system processes improvement includes a computer device having a display device and an input device each disposed in communication with the computer device. The computer device is configured to display to a user at least one virtual body part that represents a corresponding body part portion of the user requiring improvement. The virtual body part(s) is shown in a first configuration on the display device. The computer device receives user input that causes the virtual body part(s) to move in a user-directed motion. The computer device displays the user-directed motion of the virtual body part to a second configuration based on the user input. The user repeats the user input to cause improvement of physical motor control of the corresponding body part of the user.

12 Claims, 10 Drawing Sheets

Related U.S. Application Data continuation of application No. 14/891,789, filed as application No. PCT/US2014/038447 on May 16, 2014, now Pat. No. 10,603,545.

(60) Provisional application No. 61/830,465, filed on Jun. 3, 2013, provisional application No. 61/824,892, filed on May 17, 2013.

(51) Int. Cl.
*A63B 24/00* (2006.01)
*G09B 19/00* (2006.01)

(58) Field of Classification Search
USPC .......................................................... 434/257
See application file for complete search history.

(56) References Cited

U.S. PATENT DOCUMENTS

| | | |
|---|---|---|
| 5,554,033 A | 9/1996 | Bizzi et al. |
| 5,846,086 A | 12/1998 | Bizzi et al. |
| 5,984,880 A | 11/1999 | Lander et al. |
| 6,057,846 A | 5/2000 | Sever, Jr. |
| 6,098,458 A | 8/2000 | French et al. |
| 6,162,189 A | 12/2000 | Girone et al. |
| 6,164,973 A | 12/2000 | Macri et al. |
| 6,421,048 B1 | 7/2002 | Shih et al. |
| 6,749,432 B2 | 6/2004 | French et al. |
| 6,827,579 B2 | 12/2004 | Burdea et al. |
| 7,179,234 B2 | 2/2007 | Nashner |
| 7,460,125 B2 | 12/2008 | Yang et al. |
| 7,731,500 B2 | 6/2010 | Feygin et al. |
| 7,993,291 B2 | 8/2011 | Karkanias et al. |
| 8,834,169 B2 | 9/2014 | Reinkensmeyer et al. |
| 9,271,660 B2 | 3/2016 | Luo et al. |
| 9,326,909 B2 | 5/2016 | Liu et al. |
| 9,403,056 B2 | 8/2016 | Weinberg et al. |
| 9,483,622 B1 | 11/2016 | Snyder |
| 2002/0120362 A1 | 8/2002 | Lathan et al. |
| 2002/0146672 A1 | 10/2002 | Burdea et al. |
| 2004/0254771 A1 | 12/2004 | Riener et al. |
| 2004/0267320 A1 | 12/2004 | Taylor et al. |
| 2005/0250083 A1 | 11/2005 | Macri et al. |
| 2006/0074822 A1 | 4/2006 | Eda et al. |
| 2006/0084050 A1 | 4/2006 | Haluck |
| 2007/0016265 A1 | 1/2007 | Davoodi et al. |
| 2007/0048702 A1 | 3/2007 | Jang et al. |
| 2007/0126733 A1 | 6/2007 | Yang et al. |
| 2008/0009771 A1 | 1/2008 | Perry et al. |
| 2008/0132383 A1 | 6/2008 | Einav et al. |
| 2009/0221928 A1 | 9/2009 | Einav et al. |
| 2009/0326341 A1 | 12/2009 | Furlan |
| 2011/0009241 A1 | 1/2011 | Lane et al. |
| 2011/0054870 A1 | 3/2011 | Dariush et al. |
| 2012/0004579 A1 | 1/2012 | Luo et al. |
| 2012/0021394 A1 | 1/2012 | deCharms |
| 2012/0077163 A1 | 3/2012 | Sucar Succar et al. |
| 2012/0108909 A1 | 5/2012 | Slobounov et al. |
| 2012/0142416 A1 | 6/2012 | Joultras |
| 2012/0157263 A1 | 6/2012 | Sivak et al. |
| 2013/0035734 A1 | 2/2013 | Fernandez et al. |
| 2013/0046206 A1 | 2/2013 | Preminger |
| 2013/0072353 A1 | 3/2013 | Alessandri et al. |
| 2013/0096940 A1 | 4/2013 | Hayes |
| 2013/0123667 A1 | 5/2013 | Komatireddy et al. |
| 2013/0138011 A1 | 5/2013 | Ang et al. |
| 2013/0171596 A1 | 7/2013 | French |
| 2013/0252216 A1 | 9/2013 | Clavin et al. |
| 2013/0316316 A1 | 11/2013 | Flavell et al. |
| 2013/0342527 A1 | 12/2013 | Molyneaux et al. |
| 2014/0004493 A1 | 1/2014 | Macri et al. |
| 2014/0031098 A1 | 1/2014 | Tacconi |
| 2014/0147820 A1 | 5/2014 | Snow et al. |
| 2014/0364230 A1 | 12/2014 | Borghese et al. |
| 2014/0371633 A1 | 12/2014 | Evin et al. |
| 2015/0196800 A1 | 7/2015 | Macri et al. |
| 2015/0202492 A1 | 7/2015 | Domansky et al. |
| 2016/0086500 A1 | 3/2016 | Kaleal, III |
| 2016/0129343 A1 | 5/2016 | Domansky et al. |
| 2018/0214768 A1 | 8/2018 | Macri et al. |

FOREIGN PATENT DOCUMENTS

| | | |
|---|---|---|
| WO | 2011123059 A1 | 10/2011 |
| WO | 2012161657 A1 | 11/2012 |
| WO | 2013136287 A1 | 9/2013 |
| WO | 2019016811 A1 | 1/2019 |

OTHER PUBLICATIONS

Pawel Pyk et al., "A Paediatric Interactive Therapy System for Arm and Hand Rehabilitation," In 2008 Virtual Rehabilitation, IEEE, pp. 127-132.

PCT International Search Report and Written Opinion dated Dec. 17, 2021, International Application No. PCT/US2021/48436, pp. 1-8.

Macri et al., "Repairing Brain-Motor Disability," International ABI Clinical Study Czech Republic Poster, (c)2015, 1 page.

International Search Report and Written Opinion dated Oct. 14, 2014, International Application No. PCT/US2014/038447, pp. 1-14.

Lebedev M.A., et al., "Brain-Machine Interfaces: Past, Present and Future" TRENDS in Neurosciences vol. 29, No. 9, Sep. 2006, pp. 536-546.

Extended European Search Report dated Jul. 9, 2020, European Patent Application No. 19207843.4, pp. 1-9.

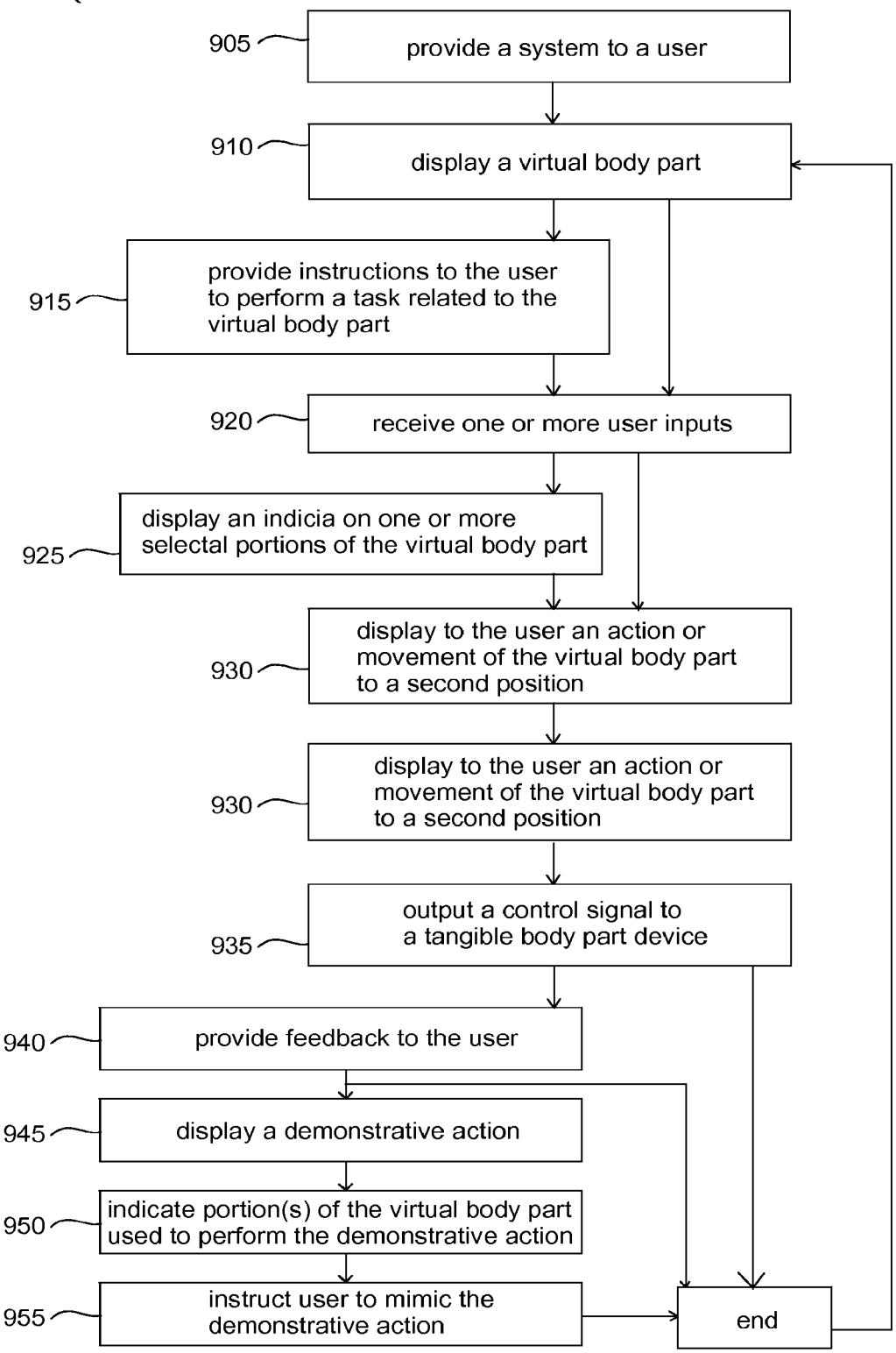

SYSTEM AND METHOD FOR PRE-ACTION TRAINING AND CONTROL

CROSS REFERENCE TO RELATED APPLICATIONS

This application is a continuation of U.S. patent application Ser. No. 16/834,614 filed May 30, 2020, which is a continuation of U.S. patent application Ser. No. 14/891,789 filed on Nov. 17, 2015, which is a National Stage of International Application No. PCT/US2014/038447 filed on May 16, 2014, which claims priority from U.S. Provisional Application No. 61/830,465 filed on Jun. 3, 2013 and U.S. Provisional Application No. 61/824,892 filed on May 17, 2013. The contents of the above applications are incorporated herein by reference in their entirety.

TECHNICAL FIELD

The present invention relates to improving physical motor control of affected human extremities and related cognitive and nervous system processes and more particularly to apparatuses, systems, and methods for achieving same.

BACKGROUND

Acquired brain injury ("ABI") includes without limitation stroke, chronic traumatic encephalopathy, spinal cord injury, and traumatic brain injury ("TBI"). Survivors of ABI or other individuals affected by any condition, disorder, or experience (collectively referred to as "survivors"), noted in this disclosure, often sustain impaired or eradicated use of one or more extremities and other body parts. The consequences include mild to severe disabilities to control physical movements or movement and actions. The disabilities exist despite, in many instances, the affected body parts being somewhat or totally physically uninjured.

For survivors, performing physical movements or movement and actions corresponding to purposeful physical movements or movement and actions they used to make is difficult or impossible. They need to self re-train/re-learn to perform movements or movement and actions before being able to move. Such self re-training/re-learning requires brain and nervous system motor control planning and command processes. However, survivors have chronic disconnections between intact and in many cases, initially uninjured body parts and non-functional or dysfunctional brain and nervous system planning and command processes required for purposeful movements of body parts. In some cases survivors' difficulties are magnified due to their being unaware that the affected body part still exists.

Conventional physical and occupational rehabilitation/therapies for treating ABIs are primarily physical in nature. They involve assisted efforts to restore survivors' abilities to make unaffected physical movement and actions. Physical and occupational therapy movement and actions are characterized by manipulations, i.e., movements of survivors' body parts, corresponding to unaffected movements. For example, when a survivor recovering from a stroke or TBI undergoes rehabilitation to regain proper axial movement of the survivor's arm at the shoulder, she/he with assistance repeatedly attempts to move (or have moved with professional or mechanical assistance) her/his arm in the axial direction. Those assisted movements are to promote recovery by assisted manipulation of extremities to make movements corresponding to movements survivors used to make without assistance. That process is predominantly control of the extremities from the outside-in.

In addition to survivors" physical and occupational rehabilitation/therapies, at least one of three other therapies is used, namely, motor imagery, mirror therapy, and movement and action-observation therapy. Motor imagery involves imagining motor controls and attempting to physically exercise the resulting imagery. Mirror therapy has been used for amputees experiencing phantom limb pain. It involves using an intact body part to make physical movement and actions reflected in a physical mirror. The mirrored movement and actions appear to be made by the contralateral (amputated) body part. The patient's observation of said movement and actions has been shown to decrease or terminate phantom limb pain. Movement and action-observation therapy is theoretically mirror-neuron-based and involves viewing physical movement and actions followed by the patient's efforts to match or imitate the observed movement and actions.

Physical or occupational therapies are based on hands-on or assisted physical manipulation. They address planning to purposefully move by physically moving extremities (an outside-in process). The therapies discussed above are imagery (synonymously "visualization") based, however imagined movements result in imagined feedback (an inside-in process).

ABI survivors' chronic disabilities require extensive rehabilitation. Survivors undergo long-term and costly physical and occupational therapies. These are major healthcare services and cost issues representing a major unmet medical need. Epidemiologically, and by way of example, the approximate number of annual survivors of ABI and spinal cord injury in the European Community (EC) is 4.4 million individuals and in the United States 2.75 million individuals. A broader category, neurotrauma (penetrating and non-penetrating), including primary brain tumor, focal dystonias, limb apraxia/ataxia, cerebral palsy and amputations, annually affects more than 19 million EC individuals, 12 million U.S. civilians and approximately 200,000-400,000 U.S. combat veterans.

SUMMARY

The following presents a simplified summary of one or more aspects of the present disclosure in order to provide a basic understanding of such aspects. This summary is not an extensive overview of all contemplated aspects, and is intended neither to identify key or critical elements of all aspects nor to delineate the scope of any or all aspects. Its sole purpose is to present some concepts of one or more aspects in a simplified form as a prelude to the more detailed description that is presented later.

The broad medical problem is that while physical movement simulations are extensively in use, individuals most in need in of care, specifically survivors and other health-affected individuals (synonymously "users") have few if any simulations and correlative physical activations tailored to their needs and none in said field. Survivors' goals may include regaining or improving processes that enable performing activities of unaffected living after, without limitation: neurological injury, disorder or condition resulting from penetrating or non-penetrating insult injury or stress; or physical injury due to invasive or non-invasive causation; or experiencing psychological or neurochemical disorder.

The access-to-care problem is that when affected by an injury, disorder or condition, the affected individual has insufficient methods and apparatuses available to activate needed brain and nervous system processes, or to stimulate, much less repeatedly stimulate, without limitation, neurons, neurological support cells, inter-neuron communications, gray and white matter cortical circuitry, other brain circuits or communications or tissues or proteins of the brain or central nervous system and contemporaneously or simultaneously activate by wired or wirelessly means at least one device attached to at least one human body part in need of rehabilitation, therapy or functional correction. The user's more particular medical, therapeutic, and rehabilitative care problems are to use methods and apparatuses of the present invention to improve the detriments noted above by controlling a virtual image(s) to simulate physical movements and movement and actions and to actuate an attached or unattached body part device such that the device activates or stimulates one or more body parts. Actuation can be accomplished, for example, by wired or wireless means.

Existing science holds that repeated stimulation of neurological receptors may form "cell assemblies" and that beneficial mathematical relationships exist between outcomes of repeated firing of interconnected neurological cells and learned behavior. Using the present invention at least includes and provides for repeated, self-induced neuronal stimulation and self-teaching, including interactive instantiation of kinetic imagery.

Physiologically, the user's challenge is to initiate or improve physical or related cognitive activities before or without being able to perform or practice partial or full physical activities. Using the present invention stimulates survivors' brain and nervous system processes to perform purposeful movements by survivor's instantiating visual images of their abstract thoughts regarding purposeful physical movements and movement and actions. They control realistic virtual extremities that have analogous true range of motion to simulate physical purposeful movements and movement and actions (an inside-out process) and by wired or wireless means actuate at least one attached or unattached physical body part device such that the physical body part device activates or stimulates one or more physical body parts.

The present invention can be used without limitation for self-teaching a) brain processes to enable performing new movement and actions or improve past movement and actions e.g. to help rehabilitate after spinal cord injury, stroke or traumatic brain injury or chronic traumatic encephalopathy patients; or b) potentiation of brain processes to replace or supplement damaged neural circuits e.g. help joint-replacement patients regain abilities; or c) de-activation of existing neuromuscular movement and actions, e.g. to decrease or stop users' uncontrolled muscle movement and actions as in focal cervical dystonia; or d) de-sensitization of damaged neural circuits e.g. phantom limb or other painful body parts; or e) creation of brain processes to supplant dysfunctional/debilitating experiences e.g. suffering from phobias, schizophrenic hallucinations or autism spectrum sensory-movement and action disorders; or f) performing or practicing partial or full body movement and actions.

For survivors/users with disabled or dysfunctional use of body parts or with psychological conditions impeding control of movement and actions or related cognitive processes, imagined movement and action alone result in imagined feedback. Visualization and imagery alone, e.g. without creating physical movement simulations and actuation of devices attached or unattached to body parts are only somewhat sufficient for improving physical motor control, movement and movement and action planning or execution or restoration or improvement of unaffected physical movements, movement and actions and/or related cognitive and nervous system processes. The present invention provides video game-like, opportunities and actuation of devices attached or unattached to body parts so that said survivor is able to transition from mere visualization to external feedback generation, i.e. to instantiate abstract mental representations of physical movement and actions into actual visual displays of simulated physical movement and actions, synonymously, "viewable embodiments of cortical simulations of physical movement and actions" and to initiate or improve or enhance actual physical movements by contemporaneously or simultaneously actuating one or more devices attached or unattached to one or more body parts. One solution to said survivors' problems in preparing for real-world physical movements and movement and actions is to use methods and apparatuses for pre-movement and action control of user-controllable images that enable control of virtual representations of body parts and contemporaneously or simultaneously control of devices attached or unattached to the user's body. One objective is to provide a method and apparatus enabling said survivor to instantiate kinetic imagery using simulations i.e. to transition from personal mental images or visualizations of physical movement and actions into instantiations of simulated physical movement and actions, synonymously, "viewable embodiments of cortical simulations of physical movement and actions" that transmit signals to devices attached or unattached to the user's body. One technical problem therefore is to control user controllable images to simulate physical movement and actions on any display screen and thereby contemporaneously or simultaneously transmit signals actuating devices attached or unattached to body parts that stimulate or actually move survivors'/users' body parts to provide said survivors'/users with both stimulating virtual alternatives (simulated physical movements), to actual physical movement and action feedback and actual physical movement.

The present invention enables negatively health-affected individuals e.g. said survivors/users, synonymously, "plurality of users," to use self-controlled and/or directed pre-movement and action training simulations, with or without professional instruction, to actuate devices attached or unattached to the user's body parts or to stimulate said body parts and brain areas and nervous system processes in order to improve capabilities for physical movement and action and related cognitive and nervous system functioning. Operationally, said survivors/users control virtual body parts that are anatomically realistic with analogous true range of motion to simulate physical movement and actions, thereby engaging in pre-movement and action training and simulations. In one aspect, the user controls at least one virtual body part contemporaneously or simultaneously actuating and controlling one or more body part devices attached or unattached to the user's corresponding or non-corresponding body part, causing said at least one body part to move and/or be stimulated. Said invention enables said user to repeat brain and nervous system stimulation in part through interactive instantiation of kinetic imagery, synonymously, "viewable embodiments of cortical simulations of physical movement and actions" and to initiate or improve or enhance physical movements.

The present invention is directed without limitation to individuals affected by spinal cord injury, severe autism, autism spectrum disorders, stroke, traumatic brain injury, focal dystonias, chronic traumatic encephalopathy, amputees, joint replacement patients, or other conditions in need of physical, occupational or psychological rehabilitation/ therapy, without limitation, brain tumors, cerebral palsy, Parkinson's disease, schizophrenia, phobias, other acquired brain injuries ("ABI"), or other medical deficits, disorders or diseases. Further operationally, before or without being able to perform partial or complete physical movements and/or movement and action(s), said user executes inputs (using any input device e.g. without limitation a wireless or wired computer mouse, touch-screen, head or eye movement and actions or brain signals) that control or direct simulated physical movement and actions of on-screen or holographic images thereby signaling actuation of the attached or unattached body part device. Said user's physical method of inputs is physically non-corresponding to displayed movement and actions of on-screen images. Said images may be static or controlled to simulate movements and/or movement and actions. Said inputs control virtual body parts, synonymously, the entire body, whether representing the user or not, clothed, skin covered, or exposed displayed in any virtual environment and the attached or unattached body part device. Said user inputs may simultaneously, contemporaneously, or sequentially control single or multiple virtual body parts and contemporaneously or simultaneously actuate at least one device attached or unattached to at least one body part of the user such that said device activates or stimulates one or more body parts.

Using the present invention, the user will attempt to create simulated and/or actual physical movement and actions and will succeed in doing so. Consequently, the user's brain and nervous system planning processes for anticipated and intended physical movement and actions and related cognitive processes are activated, stimulated and/or improved or enhanced. This activation may be followed by controlling and/or directing desired, purposeful, simulated movement and actions. Basically, users anticipate or intend to originate or otherwise cause simulated physical movements or movement and actions and know the meaning of such movements or movement and actions. Using the methods and/or apparatuses of the present invention, which include creating and/or utilizing instantiated kinetic imagery and actual physical stimulation, movement and feedback, will help to illustrate and reinforce what the user planned to do and actually did. Repetition makes it possible to do all of that better.

The one or more users of the present invention are able to transition from conscious imagery/visualization, in effect abstract mental processes, to real visuomotor feedback of simulated physical movement and actions and actual physical movement additional feedback. Accordingly, for said affected conditions, injuries, disorders or experiences, or for any user who is challenged, the present invention enables instantiation of kinetic imagery, i.e. "viewable embodiments of cortical simulations of physical movement and actions" and virtual and/or actual physical movement and action feedback for self-re-training/re-learning and self-re-exercising virtual and actual physical movement and actions or skills, i.e., self-therapy.

Embodiments described herein pertain generally to physical motor, cognitive and nervous system improvement. Some embodiments relate to assisted physiological movement to rehabilitate injured physiology. Further embodiments pertain to the field of user pre-movement and action gaming simulations, synonymously, "pre-movement and action training simulations" in conjunction with movement and action exercise, or using methods and apparatuses that provide for user control of virtual anatomical body parts and contemporaneously or simultaneously, actuation of at least one device attached or unattached to at least one human body part such that said device activates or stimulates one or more anatomical body parts. Additional embodiments pertain to the field of user pre-movement and action gaming input devices configured to provide input for pre-movement and action training in conjunction with movement and action exercise, or using methods and apparatuses that provide for user control of virtual anatomical body parts and contemporaneously or simultaneously, actuation of at least one device attached or unattached to at least one body part such that said device activates or stimulates one or more body parts.

Aspects of the present invention relate to methods and apparatuses for instantiating kinetic imagery. More particularly, the invention includes instantiating kinetic imagery by a user controlling virtual body parts alone or in conjunction with virtual objects. In an aspect, a user may engage in one or more self-teaching virtual training games, synonymously Pre-movement and action Exercise Games ("PEGs"). PEGs provide users with stimulating substitutes for actual physical movement and action feedback. Said feedback fosters stimulation of any user's brain and nervous system previously compromised due to any of the conditions or disorders listed in this disclosure or other conditions that may be within the scope of this disclosure. PEGs provide simulated physical movement and action feedback from user controlled/directed virtual body parts corresponding or non-corresponding to the user's body part(s) that may have suffered reduced or lost functionality. Said user, controlling virtual world movement and actions, is engaged in virtual training for real-world movement and actions. In an additional aspect, PEGs provide a user with a neuronal workout that stimulates without limitation neuronal recruitment, neurogenesis, synaptogenesis or brain plasticity, functions or processes.

Aspects of the present invention provide a link between kinetic visualization/imagery and user originated-controlled/directed simulated physical movement and actions. Visualization and imagery of physical movement and action is an integral step in motor planning, physical performance or reacquisition of purposeful physical movement and actions that have been compromised. The methods and apparatuses described herein implement kinetic imagery by providing each user with means to 'act out' or otherwise control virtual body parts so that the simulated movement and actions of body parts represent instantiated, real visual displays of a user's abstract processes of visualization/ imagery.

The present disclosure further relates to constructing, configuring, and/or controlling user controllable images, such as those used in pre-movement and action training. According to aspects of the present disclosure, presented is a method of constructing a user-controllable image, which includes obtaining anatomical and physiological data associated with a model of a body, storing said data in a database, and creating the user-controllable image based on said body model data, wherein the user-controllable image may be configurable to a user, wherein at least a moveable part of the user-controllable image is constructed to move based on input controls from a user, and wherein the user-controllable image is constructed so as to enable pre-movement and action self-training by a user. In an additional aspect, demonstrative movement and actions of the user-controllable image or any image(s) can be generated by using motion capture or other technologies. In an additional aspect, motion capture or other technologies can likewise be used to construct and/or configure a user controllable image.

In an additional aspect, presented herein is a method of configuring a user-controllable image to a user, which includes obtaining at least one default parameter associated with the user-controllable image, obtaining at least one user parameter associated with a user body, comparing the at least one default parameter and the at least one user parameter, constructing a user-configured, user-controllable image by adjusting one or more of the at least one default parameter where the at least one user parameter differs from the at least one default parameter, wherein the user-configured, user-controllable image is configured so as to enable pre-movement and action self-training by a user, and providing the user-configured, user-controllable image to the user for pre-movement and action training. In an additional aspect, motion capture or other technologies can likewise be used to configure a user-controllable image ("UCI").

The present disclosure further provides an example method of controlling a user-controllable image, which includes providing a virtual body part to a user, wherein the user-controllable image comprises the virtual body part, receiving a selection input or multiple selection inputs from the user, wherein said selection input(s) is associated with at least a of one or more virtual body parts, receiving a movement and action input from the user, and displaying an movement and action of the virtual body part based on the movement and action input, wherein the displayed movement and action is non-corresponding to the survivor/user's input activity(ies) and wherein the selection input(s) and movement and action input(s) are at least a part of pre-movement and action self-training by a user. In addition, the present disclosure contemplates without limitation apparatuses, computers, computer readable media, hand-held devices, computer program products. Internet accessibility, cloud computing, multi-user use and means for performing these said example methods.

The present disclosure further relates to methods and apparatuses that provide for user pre-movement and action control of non-virtual prostheses, exoskeleton body parts, robots or other motile or audiovisual devices, synonymously, "at least one non-virtual object." This disclosure provides an example method for controlling a UCI representing said at least one non-virtual object. It includes providing a virtual representation of a non-virtual object to a user, wherein said representation of a non-virtual object receives a selection input(s) from the user, wherein the selection input is associated with at least a part of the non-virtual object, wherein receiving an movement and action(s) input from the user, and displaying, approximately simultaneously, said virtual movement and action and a physical movement and action of the at least a part of the non-virtual object and based on the movement and action input, wherein the said virtual and physical movement and actions are physically non-corresponding to the movement and action input and wherein the selection input and movement and action input are at least a part of pre-movement and action training a user to use a non-virtual object.

Further aspects of the present invention relate to using pre-movement and action exercise games ("PEGs") for medical diagnostic purposes or measuring brain processes and biological substances, or biomarkers, per se or to improve PEGs. In such further aspects a health-affected survivor/user, using PEGs, simultaneously has brain processes and biological substances and/or biomarkers assessed or measured, then compared to a baseline or control value corresponding to a control group of non-health-affected users who have used or are using PEGs.

Further aspects of the present invention relate to healthcare or research professionals learning or researching "what-ifs" relating to any of the conditions to which this invention is applicable.

The methods and apparatuses of the present disclosure may be non-invasive, solo video game-like, heuristic, economical and useable on any computer or other digital device, practically anywhere and at any time. The present invention has the potential to leverage users' rehabilitation or therapists' productivity to high levels. It is well-suited to hands-on or telemedicine healthcare services.

In one embodiment of the present invention, a system for improvement of physical motor control of affected human extremities and related cognitive and nervous system processes includes a computer device having an input device and a display device each disposed in communication with the computer device. The computer device is configured to display to a user a virtual body part that represents a corresponding body part of the user requiring improvement. The virtual body part(s) optionally includes one or more selectable body part portions. The virtual body part or the selectable body part portion(s) is (are) shown in a first position or configuration on the display device. The computer device receives one or more user inputs that cause the virtual body part to move in a user-directed motion or a predefined motion. The computer device displays the predefined or user-directed motion of the virtual body part (and/or of the selectable body part portion) to a second position or configuration based on the user input. The user repeats the user input as necessary to cause improvement of physical motor control of the corresponding body part of the user and related cognitive and nervous system processes improvement.

In another embodiment of the system, the user input includes one or both of a selection input associated with the selectable body part and a movement and action input indicating the virtual movement in virtual 3D space of the body part.

In another embodiment of the system, the computer device is further configured to provide to the user an instruction to perform a task selected of moving the virtual body part in virtual 3D space, changing the position of the at least one selectable body part to a second position in virtual 3D space, moving an object in virtual 3D space, grasping a virtual object, touching a virtual object, aligning the virtual body part with a virtual object, positioning the virtual body part relative to a virtual reference point, using the virtual body part to select a virtual object, releasing an object, or rotating the virtual body part in virtual 3D space.

In another embodiment of the system, the computer device is further configured to provide to the user an instruction to perform a task of aligning the virtual body part with a displayed reference point, selecting one object among a plurality of displayed objects, or moving the at least one selectable body part to a displayed target.

In another embodiment of the system, the input device is configured to detect a biomarker or neurological signal of the user, correlate the biomarker or neurological signal to a movement and action associated with the virtual body part, and display to the user a virtual manifestation of the movement and action based on the biomarker or neurological signal.

In another embodiment of the system, the input device includes a user movement and action recognizing component configured to recognize a movement and action of the user.

In another embodiment of the system, the computer device is configured to display an indicia on the virtual body part or a portion thereof in response to the user input.

In another embodiment, the system includes a tangible body part device disposed in communication with the computer device, where the computer device is configured to output a control or actuation signal to the tangible body part device based on user input. In one embodiment, the feedback device is a tangible body part device disposed in communication with the computer device, where the tangible body part device is actuated by a sound signal from the computer device.

In another embodiment, the system includes a feedback device disposed in communication with the computer device, wherein the feedback device provides feedback to the user based on the user input, where the feedback to the user is without limitation a sound or electrical signal coupled to or communicating with a muscle or nerve of the user, tactile feedback, visual feedback, audio feedback, or an electrical or sound signal configured to control a tangible body part device disposed in communication with the computer device.

In an embodiment where the feedback is an electrical or sound signal configured to control a body part device, the tangible body part device is connected to the user. For example, the tangible body part device is operationally connected to the user. In another embodiment, the tangible body part device is not connected to the user. In another embodiment, the electrical or sound signal contemporaneously causes the body part device to substantially perform the movement of the virtual body part based on the user input.

In another embodiment of the system, the input device is configured to obtain a user measurement and compare the user measurement to a control value, where the user measurement is a neurological signal, a biological substance measurement, and/or a biomarker measurement.

In another embodiment of the system, the computer device is further configured to display to the user a demonstrative movement and action of the virtual body part, indicate to the user at least one virtual body part used to perform the demonstrative movement and action, instruct the user to mimic the demonstrative movement and action by entering at least one user selection, and receive the one user selection where the user selection(s) is (are) associated with the virtual body part used to perform the demonstrative movement and action.

To the accomplishment of the foregoing and related ends, the one or more aspects comprise the features hereinafter fully described and particularly pointed out in the claims. The detailed description of the invention and the annexed drawings set forth in detail certain illustrative features of the one or more aspects. These features are indicative, however, of but a few of the various ways in which the principles of various aspects may be employed, and this description is intended to include all such aspects and their equivalents.

BRIEF DESCRIPTION OF THE DRAWINGS

The disclosed aspects will hereinafter be described in conjunction with the appended drawings, provided to illustrate and not to limit the disclosed aspects, wherein like designations denote like elements, and in which:

FIG. 9 illustrates a flow chart of one embodiment of a method of rehabilitation of the present invention.

DETAILED DESCRIPTION

Figure 1:
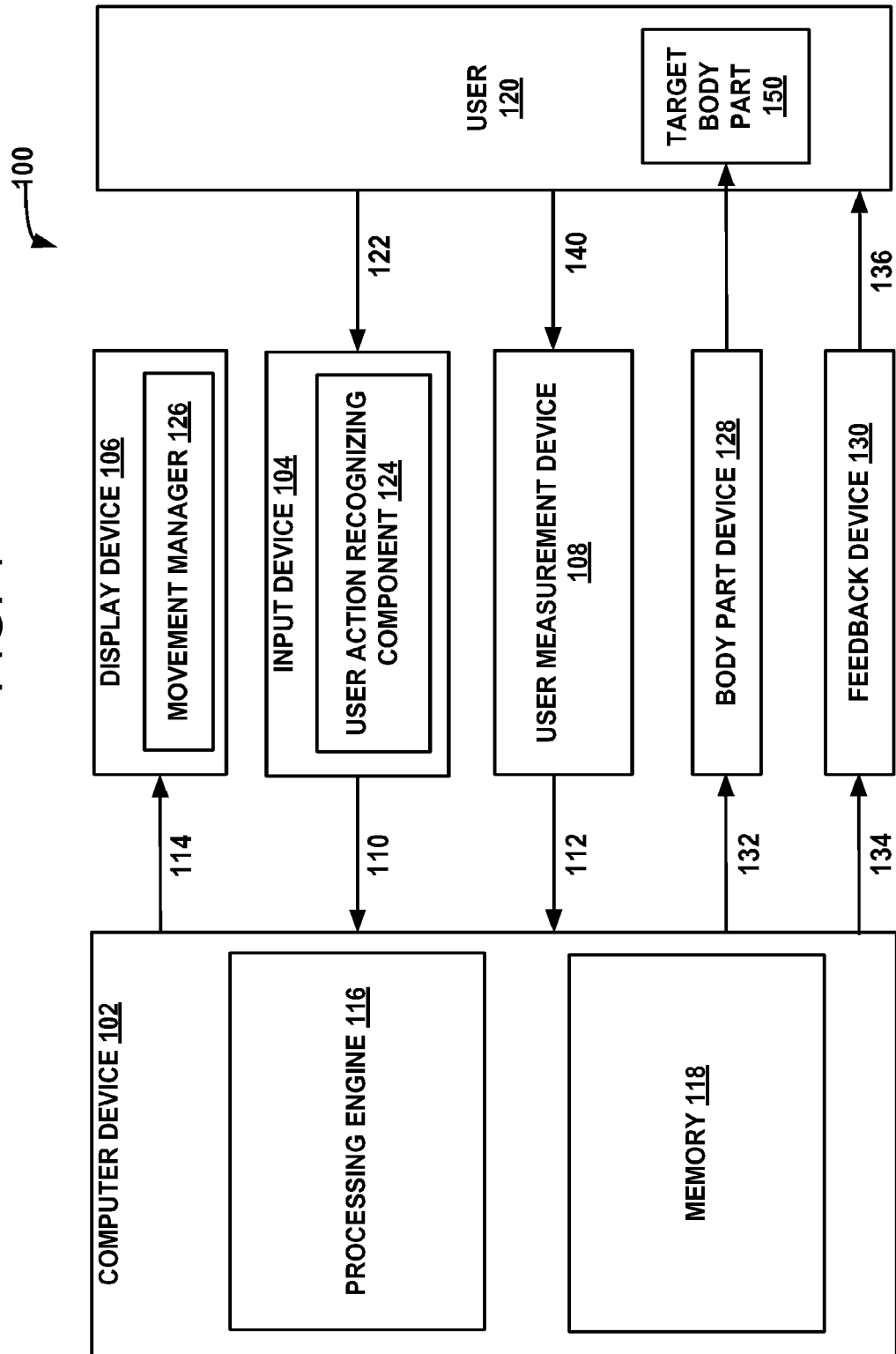
FIG. 1 is a system-level component diagram illustrating a system for assisted body part movement including actuation of at least one device attached or unattached to at least one body part such that the device activates or stimulates one or more anatomical body parts and based on pre-movement and action training according to aspects of the present disclosure.

For the purposes of this disclosure, "cognitive improvement" means the act of improving mental processes associated with purposeful physical movements and movement and actions or purposeful control of a body part of the user.

Purposeful and reflexive physical movement and actions of body parts are proximally derived from neuronal signaling (spinal cord outputs) to muscles. However, pre-movement and action planning for purposeful movement and actions is derived from neuronal signaling (brain outputs) and initiating neuronal signaling to the spinal cord. Brain communications are essential to commanding purposeful new physical movement and actions or to regaining ability to perform the physical movement and actions or related cognitive processes or to correct physical, neurological or psychological movement and actions associated with disorders or conditions.

Aspects of the present invention relate to methods and apparatuses for pre-movement and action training, also disclosed as pre-movement and action training for ABI/TBI survivors. The term ABI/TBI survivors in this disclosure includes without limitation other conditions and disorders disclosed in this disclosure and others to which pre-movement and action training may be useful. More particularly, the invention is for pre-movement and action training by ABI/TBI survivors using virtual body parts.

In an aspect, a user, who may be an ABI/TBI survivor, may engage in one or more pre-movement and action exercise games ("PEGs"). PEGs provide ABI/TBI survivors with brain stimulating substitutes for actual physical-movement and action feedback. The PEGs feedback fosters improvement of the user's pre-movement and action brain processing, including without limitation parts of the brain compromised due to the ABI/TBI. PEGs provide simulated physical-movement and action feedback from user-originated physical simulations via controlled/directed, virtual body parts corresponding to at least the user's body parts that suffered reduced or lost functionality as the result of ABI or TBI. Such survivor controlled/directed, virtual body parts are caused by the user to simulate physical movement and actions thereby executing virtual-world movements and movement and actions as pre-movement and action training for real world movements and movement and actions. In an additional aspect, PEGs provide the ABI/TBI survivor with a pre-movement and action training workout that stimulates without limitation neuronal recruitment, inter-neuron communication, neurogenesu(is), synaptogenesis, and brain plasticity.

PEGs survivors/users bridge a gap between kinetic imagery/visualization and creating user-originated/directed simulated physical movement and actions. Imagery/visualization of physical movement and actions is integral to movement and action planning, physical performance, and reacquisition of physical movements, movement and actions and/or skills. The methods and apparatuses described herein support kinetic imagery/visualization by providing each user with means to "act out" or otherwise control virtual body parts so that the body parts represent real visual instantiations of a user's abstract processes of imagery/visualization.

PEGs are without limitation exercises used in pre-movement and action control/direction of virtual body parts to simulate physical movement and action intentions and at least to receive feedback for neuro-improvement of movement and action-planning processes.

According to aspects of the present disclosure, intermovement and action with virtual body parts links any user's cognition, visualization, or imagery to virtual movement and action feedback. Furthermore, the methods and apparatuses described herein can engage ABI/TBI survivors to self-teach movement and action planning for purposeful physical movement and actions.

According to aspects of the present disclosure, an ABI/TBI survivor may target and help overcome her/his movement and action deficits by making inputs to a system that displays a user-controllable virtual body part, thereby directing and causing simulated movement and actions of all or a moveable region of the virtual body part based on the inputs, viewing feedback from such simulated movement and actions and improving and/or building new and/or re-building impaired neurological or brain processes.

According to the present disclosure, any user may control and direct any virtual body part(s) to display simulated, human physical movements and movement and actions with virtual full range of motion. The user may control a virtual body part to speed up, slow down, stop or make any combination of the movement and actions or gradations of same. System displays of virtual body part movement and actions may be idiosyncratic representations of each survivor's input controls and direction. In effect, the user's virtual body part control process stimulates cognitive processes and pre-movement and action-training for real movement and action processes.

In an aspect, a computer device may control and display virtual movement of the virtual body part and may transmit one or more signals to a (tangible) body part device, which may stimulate one or more body parts of the user to move, for example, in a way that may correspond to the movement of the virtual body part. In some examples, the body part device may initiate body part movement by stimulating one or more receptors or triggers of the user's neurological system, which may in turn cause movement of the muscles, tendons, tissue, or any other part of the user's body.

Furthermore, the methods and apparatuses presented herein differ from modern gaming systems like Wii™ and Kinect™ that are being used for physical and occupational rehabilitation. Said systems require their users to make actual physical movement and actions that are then displayed in virtual environments. Therefore, by design, Wii™ and Kinect™ users make actual physical movement and actions that correspond to displayed movement and actions. Conversely, the methods and apparatuses presented herein eliminate the requirement of user performance of corresponding physical movement and actions to what are then displayed as simulated physical movement and actions.

For example a user of the present invention can make small or limited non-corresponding wired or wireless eye and/or head gestures carried by webcam signals or brain signals, to control the simulated movement and actions of virtual body parts. In but one example, any user's input signals by eye controls (alone) can direct a virtual shoulder to move a virtual arm ninety degrees away from the virtual body. Accordingly, a user's input signaling processes associated with the present invention are non-corresponding to the simulated movement and actions of the virtual body part. That is, a user's physical method of input, e.g., movement of a wired or wireless mouse, or eye or head movements or transmission of a wired or wireless brain signal from the user, does not correspond to the simulated physical movements and movement and actions of the virtual body parts of the present disclosure.

The manner of inputs (controls and directions) described herein are dissociated from displayed virtual-image movement and actions and allow ABVTBI survivors to cause simulated physical movements and movement and actions before and without performing actual physical training movement and movement and action processes. Each user's inputs according to the present disclosure are not physical-training movements and actions of the desired drill or skill. Rather, the present methods and apparatuses target without limitation neuronal systems, brain structures, gray and white matter circuitry, neurogenesis, synaptogenesis, myelination, brain plasticity, and cognitive processes, not any particular physical action inputs.

Physical training participation, due to its repetitive aspects, can be tedious and hindered by boredom. Participation in physical training is also fraught with the chance of new injury or aggravating old injury. PEGs provide entertaining, rewarding, and immersive features, including game sequence movement and actions that result from a user's successful control, direction, and manipulation of virtual body parts in addition to control, stimulation, or manipulation of a body part device or object, a non-virtual robot, prosthesis, or exoskeleton.

For example, in terms of non-limiting and non-exclusive variations of research and investigation as well as practical application, monitoring brain activity can enhance PEGs' pre-movement and action training value. ABI/TBI survivors' brain activities or processes can be measured through any brain imaging technology or by analyzing blood and/or other body fluids, or biomarkers, or other substances for particular bio-chemicals, markers, and/or compounds related to without limitation overall brain cortical, or cognitive activity. Biomarkers include but are not limited to pulse rate, blood pressure, respiration rate, perspiration, body temperature, and eye dilation. Typically, biochemical levels and neurological signals may be measured or monitored to detect a spike or change in the level in response to an event or stress.

ABI/TBI survivors' baseline brain activities or processes could be determined before, during and after PEGs training to measure changes accompanying PEGs training. For example, a signal peak, amplitude value, numerical value, concentration, timing of a signal, length of a signal, and other signal characteristics can be observed and compared with baseline values, threshold values, or ratios. Based on these observations, one may draw conclusions regarding the progress of the individual in restoring or improving a deficit or diagnose conditions, such as TBI, in a subject. Additionally, ABI/TBI survivors' brain activities or processes can be compared to non-ABI/TBI affected individuals undergoing or who underwent PEG training activities to determine whether PEG training is stimulating the same or similar affected parts of the ABI/TBI survivors' brains as are stimulated in the non-ABI/TBI affected individuals' brains. PEGs can be adjusted accordingly to enhance the brain activity or processes in the identified brain structures, processes or circuitry of the ABI/TBI survivors to match brain activities (including substance quantities, levels, and the like) of non-affected individuals' brain structures, processes or circuitry accompanying PEGs training. Other non-limiting and non-exclusive variations on the process are discussed below.

PEGs can also be used as a non-invasive diagnostic tool. Some ABI/TBI survivors suffer mild brain injury; however, current diagnostics are limited, comprising mostly subjective tests and some technical means. Additionally, while moderate to severe ABI/TBI is detectable through changes in brain morphology by CT-scans, MRI or other imaging technologies, mild ABI/TBI is difficult to detect or diagnose. Any survivor, who does not show severe or moderate TBI, could also be introduced to playing PEGs to monitor for mild ABI/TBI. Potentially mildly affected patients would play PEGs, and her/his brain activities would be compared to unaffected individuals' baseline brain activities to determine the comparative state or extent of mild injury or the possibility of unlikely or no detectable injury. PEGs may be used for assessing other levels of ABI/TBI, either solo or in conjunction with other methods or devices.

Various aspects are now described with reference to the drawings. In the following description, for purposes of explanation, numerous specific details are set forth in order to provide a thorough understanding of one or more aspects. It may be evident however, that such aspect(s) may be practiced without these specific details.

Turning to FIG. 1, a system 100 is presented for presentation and manipulation of a virtual body part as means for pre-action (synonymously pre-movement), training a user. In an aspect, system 100 may include a computer device 102, an input device 104, a display device 106, and a user measurement device 108. Additionally, system 100 may optionally include a body part device 128 and/or a feedback device 130. According to an aspect, computer device 102 may be configured to receive and process one or more user inputs 110 from input device 104, one or more user characteristics 112 from user measurement device 108, and may also be configured to generate and transmit one or more display control messages 114 to display device 106. In addition, computer device 102 may be configured to execute manipulation of a displayed virtual body part based on at least the inputs 104 of user 120.

Furthermore, computer device 102 may include a processing engine 116, which may be configured to receive, process, and transmit signals associated with display, control, and/or behavior of a virtual body part (discussed below and shown in FIG. 6 by way of example). Additionally, computer device 102 may include a memory 118, which may be configured to store user characteristics (such as neurological or chemical characteristic values observed and/or measured from a user 120) and/or instructions for executing one or more PEGs.

In an aspect, input device 104 may be configured to receive one or more physical or non-physical inputs 122 from a user 120 and process and forward the processed physical inputs to computer device 102 as inputs 110. In an aspect, input device 104 may be any means of receiving direct physical input from a user 120, such as, but not limited to a keyboard, mouse, touch pad, smart phone, laptop, smart phone, computer, or generic computing device, a microphone, an input device that senses input without intervention of the user, etc. In one example, input device 104 detects commands spoken by user 120. Alternatively or additionally, input device 104 may be a device configured to generate input 110 by recognizing and processing one or more user movement and actions at user movement and action recognizing component 124, such as a movement detector, eyewear (e.g., Google glass), or headgear. For example, in an aspect, user movement and action recognizing component 124 may be configured to recognize user inputs via, by non-limiting example, eye movement and action, nominal physical movement and action of hands or other body parts, blinking, nodding, and/or by detecting and monitoring neurological signals generated by the user's body. For example, user movement and action recognizing component 124 may include a component capable of reading instructions signaled in the brain, spinal cord, or any other neurological circuit or tissue of the user 120.

Furthermore, display device 106 may be configured to display a virtual body part and movement and actions of the virtual body part. In an aspect, display device 106 may display the virtual body part visually on a screen or display, such as, but not limited to, a computer monitor, projector, television, or the like). Alternatively or additionally, body part device 128 may receive one or more external body part control signals 132, which may cause the body part device 128 to move, for example, by mechanical means. In an aspect, body part device 128 may be, but is not limited to being, a robotic arm or shoulder, prosthetic limb, or the like. In some examples, the body part device 128 may stand alone and be placed in a location viewable by the user 120. Additionally, the external body part device may be attached to the user 120, which may allow the user to witness more "true to life" movement and actions associated with his or her physical inputs 122.

In an additional or alternative aspect, body part device 128 may be configured to receive one or more control signals from computer device 102 corresponding to the virtual movement of the virtual body part being manipulated by user 120. Based on the one or more control signals, the body part device 128 may process the control signals and stimulate one or more target body parts 150 of the user 120 (or of a non-user (not shown)) to prompt movement of one or more body parts, which may include target body part 150.

In yet another aspect, system 100 may include a feedback device 130 configured to provide feedback 136 to the user 120. In an aspect, feedback device 130 may receive one or more feedback control messages 134 related to the feedback device from computer device 102, which may govern the movement and action and behavior of the feedback device 130. In an aspect, feedback 136 may include, but is not limited to, force feedback, pneumatic feedback, auditory or visual feedback, tactile feedback, non-force feedback, or any other form of feedback that may indicate an output of computer device 102 related to pre-movement and action training. For non-limiting example, feedback device 130 may be a mechanical device that a user may attach to his or her hand or arm that may provide force feedback to the user's hand or arm in order to bend the user's wrist. In such an example, this bending may occur where the user selects a virtual wrist on display device 106 and moves the virtual wrist up and down (or in any direction) by moving input device 104. Based on this input, processing engine 116 may generate and transmit a feedback control message 136 to the feedback device 130—here, the mechanical device-which may provide a force to the user's wrist to move it substantially in unison with the movement and action of the virtual image, which may be displayed on display device 106 concurrently.

As another non-limiting example, feedback device 130 can be a haptic device (e.g., a haptic mouse, belt, vibration alert, electroactive polymer, piezoelectric wave actuator, electrostatic or subsonic audio wave actuation, or electrovibration) or an electrical feedback device in contact with the user (e.g., an electrode, conductive mat, conductive garment, etc.).

In an additional aspect, system 100 may include a user measurement device 108, which may be configured to measure one or more user characteristic values before, during, and/or after engaging in pre-movement and action training activities. In some examples, user characteristic values may include without limitation neurological or chemical data, pulse, blood pressure, body temperature, pupillary dilation, perspiration, respiration rate, or any other measureable characteristic or physical parameter of an animal, which may include a human being. In an aspect, user measurement device may utilize imaging technology to measure these user characteristics, and such imaging technologies may include, without limitation. Magnetic Resonance Imaging (MRI), Functional Magnetic Resonance Imaging (fMRI), Computed Tomography (CT), Positron Emission Tomography (PET), Electroencephalography (EEG), Magnetoencephalography (MEG). Near-infrared spectroscopy (NIRS), and High Density Fiber Tracking (HDFT).

In a further aspect, user measurement device 108 may send the measured user characteristic data 112 to computer device 102 upon measurement. There, the user characteristic data may be (a) stored in memory 118 for later use or (b) fed to processing engine 116 as feedback data that processing engine 116 may utilize to alter an ongoing pre-movement and action training activity, such as an ongoing PEG, or may be used to diagnose a medical condition. Alternatively, where the user characteristic data is stored in memory, such data may be used to tailor future pre-movement and action training activities to the user's individual characteristics or current skill level or to track the progress of a user over time, or to improve PEGs.

Figure 2:
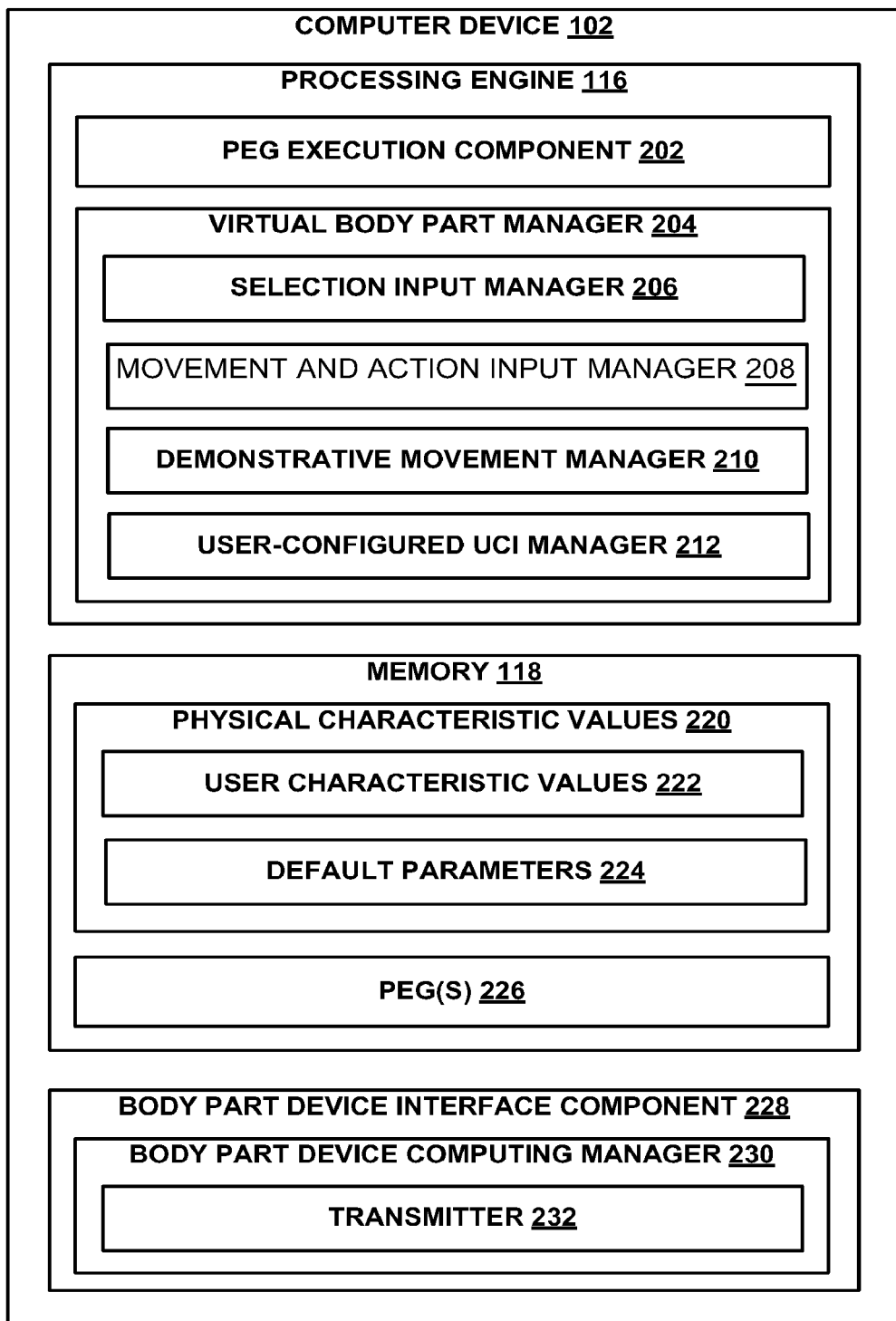
FIG. 2 is a component block diagram of aspects of a computer device for the assisted body part movement based on pre-movement and action training according to aspects of the present disclosure.

Turning to FIG. 2, an illustration of components comprising computer device 102 (FIG. 1) is provided. In operation, computer device 102 may present an initial or default virtual body part to a user, for example, when the user, trainer, coach, therapist, or any other user initially boots up computer device 102, selects a PEG 226 for pre-action training activities, or the like. To display this default virtual body part, virtual body part manager 204 may query memory 118 for default parameters 224 of a set of physical characteristic values 220 stored thereon and may process and display the default virtual body part by sending, for example, one or more display control signals to a display. In addition, once the user begins a pre-action training session, computer device 102 may receive inputs from the user, such as, but not limited to, selection inputs and movement and action inputs. Based on these one or more inputs and pre-stored and executable PEGs 226 located in memory 118, the computer device may present a selectable, movable, and otherwise interactive virtual body part with which a user may engage to partake in pre-action training activities.

As previously outlined, computer device 102 may include processing engine 116 and memory 118—the operation and composition of which will be explained in reference to FIG. 2. First, processing engine 116 may be configured to process one or more input signals and transmit the processed signals to a display device for presentation of a user-controllable image, such as a virtual body part, to a user. For purposes of the present description, a user-controllable image (UCI) may be all or part of a virtual body part or object controllable by user input to simulate physical movement and actions, wherein these physical movement and actions are non-corresponding to the user's physical movements and actions in generating the user input. Examples of UCIs described herein may comprise a virtual body part or virtual body parts, but the scope of such examples should not be limited thereto.

In an aspect, processing engine 116 may include a PEG execution component 202, which may process user inputs to generate display control messages according to instructions related to one or more PEGs. In a non-limiting example, a user may select a particular PEG to play and as a result, PEG execution component 202 may load the PEG instructions from PEGs 226 stored in memory 118. After loading the PEG, the PEG execution component 202 may generate one or more display control messages for transmission to a display device based on the PEG and any input messages received from an input device. Furthermore, in an aspect, PEG execution component 202 may be configured to alter one or more PEGs based on feedback from a user measurement device. In a non-limiting example, PEG execution component 202 may receive an indication that a user's neurological system is stronger than in the past and may make playing a particular PEG more difficult to maximize further neurological improvement.

In an additional aspect, processing engine 116 may include a virtual body part manager 204, which may be configured to virtually construct and manage movement and action of a virtual body part that computer device 102 may generate for display on a display device. Furthermore, for purposes of the present description, the term "display device" may correspond to display device 106, body part device 128, feedback device 130, or any other device or means capable of producing output corresponding to a movement and action, and/or status of a virtual body part, including output resulting from user input during pre-movement and action training activities.

In an aspect, virtual body part manager 204 may include a selection input managing component 206, which may be configured to receive one or more selection inputs from a user or an input device manipulated by a user, wherein the selection inputs may correspond to a user selecting a virtual body part or a part thereof. Furthermore, based on a selection input, selection input manager 206 may map a select location associated with a selection input to a virtual body part or a part thereof, which may correspond to a virtual body part selected for subsequent or concurrent movement and action by the user.

Furthermore, virtual body part manager 204 may include a movement and action input manager 208, which may be configured to receive one or more movement and action inputs from a user and generate one or more display control signals that cause displayed movement and action of the virtual body part. In an aspect, this displayed movement and action may correspond to the virtual body part or part thereof selected by the user and mapped by selection input manager 106. Additionally, movement and action input manager 208 may generate and display the displayed movement and action without limitation based on the user "dragging" "pointing" "tapping" "touching" or otherwise correctly manipulating at least a part of the virtual body part that is movable in virtual 3D space.

Furthermore, movement and action input manager 208 may base its virtual body part movement and action generation and/or other processing movement and actions on a particular PEG, which may have been pre-selected by a user and loaded for execution by processing engine 116. In an aspect, an movement and action input may be input by a user and received by computer device 102 as a result of the user partaking in such a PEG, other pre-movement and action training activity, or any other pre-movement and action training activity. Additionally, in an aspect of the present disclosure, a user input movement and action may be physically non-corresponding to the desired or eventual movement and action of the displayed virtual body part with which the user is interacting. For purposes of the present disclosure, a non-corresponding movement and action may be a user movement and action that differs relatively significantly from a displayed movement and action by the virtual body part.

For non-limiting example of a non-corresponding movement and action, suppose a user who is engaged in a pre-movement and action training activity wishes to move a virtual forearm directly upward using a mouse as an input device. To do so, according to aspects of the disclosure, the user may first navigate a cursor and click a mouse button to select the virtual forearm on a display device, thereby inputting a selection input. Next, the user may keep the cursor on the virtual forearm and may hold the mouse button down to signal a beginning of a movement and action input. Thereafter, the user may drag the mouse two inches along a mouse pad, with the mouse button held down, and may observe the virtual forearm rise upward, for example, from a virtual hip area to a virtual head area. To carry out this movement and action, the user's real forearm may have moved approximately two inches in a direction parallel to the mouse pad, but resulted in a virtual movement and action of the virtual forearm that was upward in direction and appeared greater than two inches in magnitude. Therefore, this example user input movement and action is non-corresponding to the movement and action of the virtual body part.

Additionally, virtual body part manager 204 may include a demonstrative movement and action manager 210, which may be configured to provide control messages to a display device to effectuate a demonstrative movement and action of the virtual body part. For example, demonstrative movement and action manager 210 may store and/or execute a retrieved demonstrative movement and action to be displayed to the user as a "ghost" movement and action. In an aspect, the user may view the demonstrative movement and action and may then attempt to manipulate the virtual body part to mimic the movement and action of the demonstrative movement and action or ghost movement and action.

Furthermore, virtual body part manager 204 may include a user-configured UCI manager 212, which may tailor or otherwise configure a displayed virtual body part to a user's body and/or alter the behavior of the displayed virtual body part based on one or more user characteristic values 222. In an aspect, such characteristics may include anatomical and physiological data characteristic values associated with the user, such as without limitation height, weight, dimension (e.g., arm length), muscle mass, TEI-affected body parts, handedness, age, gender, eye/hair/skin color, and the like. In additional or alternative aspects, the user characteristics may include historical PEG performance data associated with the user, current neurological or chemical measurement characteristics or parameter values, or the like.

In an aspect, user-configured UCI manager 212 may obtain these user characteristic values 222 from memory 118. Alternatively, user-configured UCI manager 212 may obtain these user characteristic values from a source external to memory 118, such as, but not limited to, a user measurement device configured to measure neurological and/or chemical characteristics of the user during pre-movement and action training activities, by querying a user or the user's trainer, doctor, coach, therapist or rehabilitation specialist for such characteristic values and receiving a characteristic value input in response, or otherwise receiving user-specific performance, anatomical, physiological, or other characteristic values. In another aspect, UCI manager 212 obtains user characteristic values 222 by using anatomy recognition software known in the art, such as WII™ or Kinect™, capable of detecting and identifying body parts and characteristics of human anatomical features.

In addition, user-configured UCI manager 212 may be configured to compare the user characteristic values, or user parameters, to one or more default parameters 224 stored in memory 118. In an aspect, default parameters 224 may comprise the parameters of a default virtual body part of the present disclosure, and may include without limitation anatomical and physiological data (e.g. handedness, strength, bone length, limitations on range of motion, skin characteristics, and the like). Such characteristics may conform the behavior and attributes of the default virtual body part displayed to a user before tailoring, configuring, or otherwise customizing the virtual body part to the user. In order to perform such customization, the user-configured UCI manager 212 may compare the obtained user characteristic values (e.g. user characteristic values 222) to default parameters 224. In an aspect, where the comparing determines that a user characteristic value differs from the default parameter value for a characteristic, the user-configured UCI manager may set the compared parameter of the virtual body part to be displayed to the user's characteristic value. Alternatively, where an obtained user characteristic value does not differ from the default parameter, user-configured UCI manager 212 may leave the compared parameter unchanged.

In an additional aspect, processing engine 116 may be configured to generate and/or transmit one or more display control signals to the display device to effectuate movement and action of the virtual body part. Furthermore, processing engine 116 may be additionally configured to calculate and/or report a movement and action degree or movement and action magnitude associated with a movement and action of the virtual body part. In an aspect, processing engine 116 may display the calculated movement and action degree or movement and action magnitude by generating one or more display control messages, which may be generated and transmitted in substantially real time, for transmission to a display device for visual indication of the movement and action degree to the user.

Furthermore, computer device 102 may include a memory 118, which may be configured to store information for utilization by other components in a system, such as, but not limited to, processing engine 116. Such information may include physical characteristic values 220, which may include user characteristic values 222 associated with one or more users and/or default parameters 224 associated with a baseline or default UCI, such as a virtual body part. Furthermore, memory 118 may store neurological, chemical, or any other data related to a user's body (e.g. without limitation neurological signaling data or maps, neuron activity data, etc.) generated and/or observed by a user measurement device before, during, and/or after a user engaging in pre-movement and action training. Such data may also be fed back to processing engine 116, which may alter a current or future PEG or pre-movement and action training activity based on the feedback.

In an additional aspect, such user data may be used to diagnose one or more medical conditions. For example, computer device may output the user data to a physician or other professional, who may analyze the data and diagnose the medical condition. In an alternative or additional and non-limiting example, computer device 102 may contain instructions executable by processing engine 116 to automatically diagnose a medical condition based on the user data stored on memory 118.

In addition, memory 118 may include executable instructions (e.g. executed by processing engine 116), that when performed, allow the user to engage in one or more pre-movement and action training activities. As used herein, pre-movement and action training activities may include interactive electronic games or activities, such as, but not limited to, pre-action exercise games (PEGs) 226. The PEGs 226 may govern the behavior of a virtual body part in response to one or more inputs by a user during pre-movement and pre-action training/learning activities.

Additionally, cognitive and nervous system functions are involved in all PEGs. According to some example PEGs, virtual upper body parts are presented to a user to control in order to simulate purposeful physical movements and actions—for example, opening and closing a virtual hand. Some PEGs may be virtual task games, which may couple player control of virtual body parts and objects to accomplish tasks and/or solve problems—for example, dropping a virtual spoon into a virtual cup.

Furthermore, by non-limiting example, PEGs may include upper extremity exercises including player control of any part or all of a virtual affected hands, fingers, lower or upper arm (right or left), thereby executing flexion/extension, supination/pronation, abduction/adduction, or any other body part movement and action in any direction. According to the PEGs contemplated herein, users can manage displays of some of, the majority of, or all of a virtual upper extremity from substantially any angle. Additionally, the virtual body part may comprise fingers, which may be manipulated individually or in combination. The virtual body part may comprise a wrist, which may be flexed/extended, abducted/adducted, or supinated/pronated. Furthermore, according to some non-limiting example PEGs, the virtual body part may comprise an arm, wherein the lower and upper arm may be manipulated independently or in combined movement and action of any and all joints of the arm, wrist and hand.

In non-limiting examples of some PEGs play, where the virtual body part is a virtual hand controlled in conjunction with virtual objects, the movement and action of the virtual body part may include:

thumb and forefinger pincer movement and action to grasp a key two finger movement and action to grasp a ball and drop it into a cup multi-finger movement and action to pick up a spoon and drop it into a cup full hand grasp around a mug handle full hand grasp around a mug handle at one location followed by moving the mug to a second location tapping movement and actions by index and middle fingers on a remote controller hand grasps of objects shaped as stars, circles or squares, then placement in similarly shaped slots.

Regarding virtual body parts in some non-limiting example PEGs where the virtual body part includes a virtual arm and/or a virtual hand, example games for pre-action training may include:

opening a correct box, e.g., selecting and opening the correct numbered and colored box (e.g. purple 24) in a circle of nine boxes, after applying one or more rules or condition to be met. For example, a rule or condition requires the user to make observations and computations as elementary as choosing the (single) "lowest purple box bearing an even number" (where purple 24 is correct) to computations based on several numbered boxes, e.g. "choose the highest blue even numbered box, subtract the second of its numbers from the first, square it and find the green box with that result" (if 92 blue is selected the subtraction yields number 7, which when squared is 49, so green box 49 is correct)

same as above, nine box game with audible (e.g., voice) or visible (e.g., displayed message) instructions being provided to the user/player similar open the box game in a more elementary vertical presentation of five boxes light bulb game requiring the player to unscrew a light bulb, choose the correct lettered socket and screw the bulb into the correct socket playing card games, for example in a simple game the virtual arm and hand are controlled to select a pair of twos, place that pair, right side up on a surface, then the player must choose the lowest numbered pair that wins over a pair of twos, alternately the highest numbered pair that wins over twos, then both the lowest and highest pair of picture cards that wins over twos and so forth, to more complex combinations of playing cards/hands puzzle games in which the cursor is used to move 6, 9, or 16 puzzle pieces to assemble a complete representation of any display noted above. For example, a hand image, in any orientation, position and configuration may be disassembled by the puzzle game into 6, 9 or 16 puzzle pieces to be reassembled by the player, or a more complex disassembly of the nine box arm game may be "puzzled"

simple number game displaying 0-9 and processes (add, subtract, multiply, divide and equals signs) and calling for the PEGs player to use a virtual arm and hand to select numbers and processes and to make any number of computations by arraying the numbers and processes accurately simple letter game displaying all letters of the alphabet and calling for the PEGs player to use a virtual arm and hand to select letters to make any number of words by arraying the letters accurately.

Where the virtual body part is at least one virtual muscle, games for pre-movement and action training may include selection of at least one virtual muscle to cause it to contract or relax at any rate of speed or to stop, for non-limiting example to end cramping or relieve focal cervical dystonia contractions or to regain movement impeded by hand dystonia. Therefore by loading and/or executing the one or more stored PEGs 226 of memory 118, computer device 102 may present a user with a UCI, such as a virtual body part, with which the user may interact to participate in pre-movement and pre-action training activities.

In a further aspect, computer device 102 may include a body part device interface component 228, which may be configured to interface with an external (or integrated) body part device 128, generate one or more control signals based on the user control of the virtual body part, or UCI, and transmit the one or more control signals to the body part device 128 of FIG. 1 for eventual stimulation of a target body part 150. In some examples, body part device interface component 228 may include a body part device computing manager 230 which may generate the one or more control signals based on the user control of the virtual body part. In a further aspect, the body part device computing manager 230 may include a transmitter 232, which may be communicatively coupled to the body part device 128 via a communicative connection, and may be configured to transmit the one or more control signals to the body part device 128. In some examples, the transmitter 232 may transmit the signals wirelessly or via a transmission line, depending on whether the computer device 102 is tethered to the body part device 128 via a transmission line, such as a bus or other wire. For example, where the computer device 102 is connected to the body part device 128, the transmitter may be configured to transmit the control signals over the transmission line (though it may also transmit the control signals wirelessly as well). Alternatively, where the computer device 102 is not tethered to the body part device, the transmitter 232 may transmit the one or more control signals wirelessly. As such, transmitter 232 may comprise one or more antennas or transceivers.

Figure 3:
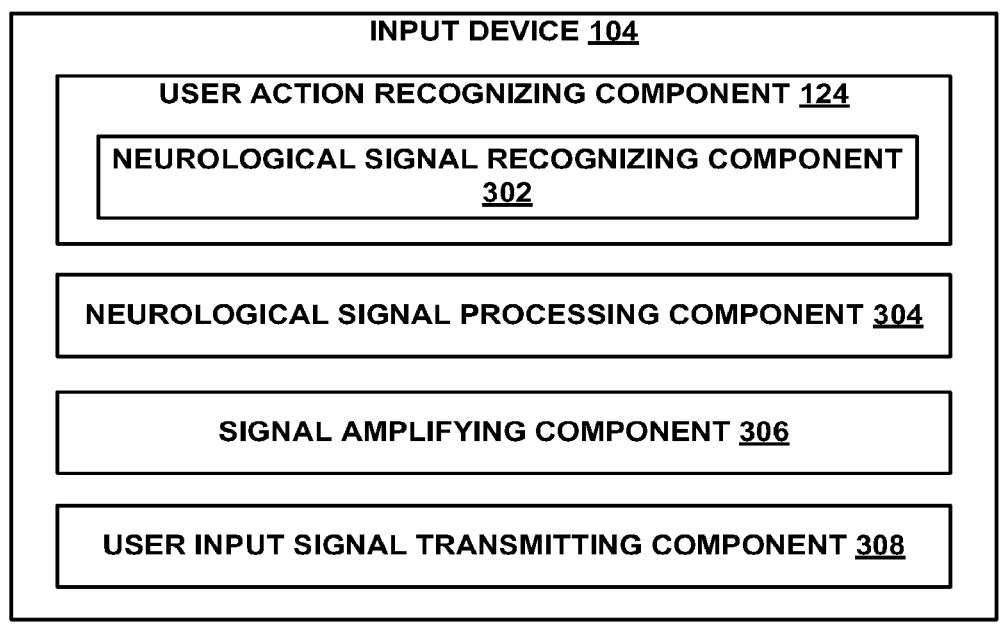
FIG. 3 is a component block diagram of aspects of an input device for the assisted body part movement based on pre-movement and action training according to aspects of the present disclosure.

FIG. 3 illustrates an example input device 104 for recognizing one or more neurological signals of a user, processing the neurological signals, and transmitting a related input signal to a computer device as input. In some examples, input device 104 may comprise a brain-computer interface (BCI), mind-machine interface (MMI), direct neural interface, or a brain-machine interface (BMI), or any other interface, neurological signal detection device, or component known to one of ordinary skill in the art capable of providing input to a computer device based on neurological signaling. In some examples, the neurological signals may be received or detected from a user's brain, a user's spinal cord, or any other neurological pathway in the user's body. Furthermore, input device 104 may include a headset or other external device that is configured to be affixed to a user's body, such as to the user's head, torso, back, arm, hand, foot, knee, leg, foot, toe, finger, such that neurological signals may be received by one or more sensors attached to the external device.

Additionally, in an aspect, input device 104 may include user movement and action recognizing component 124, as introduced above in relation to FIG. 1. In some examples, user movement and action recognizing component 124 may include a neurological signal recognizing component 302, which may be configured to recognize or detect, for example, invasively or non-invasively, neurological signals that may cause a virtual image and/or a related body part device to move based on the neurological signals. For example, neurological signal recognizing component 302 may comprise one or more neurological signal sensors, such as cortical sensors or other brain-wave sensors known to one of ordinary skill in the art. In an aspect, these sensors may be affixed directly to the user or a body part thereof, such as the brain, the spinal cord, or the like, or may be located proximately close to the user or the body part (e.g. above the skin or hair), such that the sensors may recognize or sense the neurological signal by non-invasive means.

Furthermore, user movement and action recognizing component 302 may include a neurological signal processing component 304, which may be configured to process a recognized or detected neurological signal. For example, in an aspect, the neurological signal processing component 304 may be configured to correlate the neurological signal to movement of one or more virtual images, virtual body parts, cursors, or other displayed objects being observed by the user. For example, in a non-limiting example, where a virtual hand is observed by the user on a display, the user may attempt to select a part of the virtual hand, such as a finger, and move the finger in a flexor (or other) motion. This attempt to select and/or move the part of the virtual hand may cause the user's brain and associated neurological circuitry to produce neurological signals corresponding to signals that would move a corresponding part of the user's hand, which, in some aspects, may no longer be present on the user's body. However, the neural pathways associated with such hand movement may still be present in the user's brain and body. The neurological signal processing component may process these neurological signals to correlate to an associated virtual movement of the virtual image being displayed. Alternatively, the neurological signal may be non-corresponding to actual movement of the no-longer-present body part but may instead be related to neural selection of a displayed cursor. For example, the user may select the cursor in the user's brain and use mental processes to move the cursor to a virtual body part, select the body part through a mental selection process, and move the body part (e.g. a flexor movement of a displayed virtual finger).

Such processing by neurological signal processing component 304 may comprise executing, via one or more processors, one or more instructions stored on a computer-readable medium. In an aspect, neurological signals (e.g. those recognized by user movement and action recognizing component 124 or neurological signal recognizing component 302) may be correlated to one or more control signals for altering the virtual image (e.g. selection, movement, etc.) by means of a look-up table or other stored correlation information.

In a further aspect, to allow sufficient signal strength to effectuate interface with a computer device (e.g. computer device 102 of FIG. 1), input device 104 may include a signal amplifying component 306, which may be configured to amplify the voltage of neurological signals to signal levels that may be input to the computer device as user input signals. In an aspect, signal amplifying component 306 may comprise one or more digital or analog amplifiers known to those of ordinary skill in the art. Furthermore, input device 104 may include a user input signal transmitting component 308, which may be configured to transmit the processed and amplified neurological signals, or user input signals, to one or more computer devices to effectuate virtual or non-virtual movement of a virtual or non-virtual body part. In some examples, user input signal transmitting component 308 may include a wired or wireless transmitter or transceiver, and may include one or more transmission antennae and related circuitry.

In one embodiment, body part device 128 is configured for stimulating one or more target body parts 150 of user 120 based on one or more control signals received from computer device 102. For example, the body part device 128 may be configured to transmit electrical stimulation signals to one or more neurological triggers (e.g. nerves, nerve endings, receptors, etc.) associated with the body part (e.g. a muscle, tendon, or other tissue capable of moving one or more body parts, such as a finger, arm, joint, bone, leg, toe, foot, mouth, facial muscle, shoulder, or any other body part).

For example, in an aspect, body part device 128 may include a data receiving component 302, which may be configured to receive one or more control signals transmitted by computer device 102. In some examples, data receiving component 302 may be configured to receive the control signals wirelessly or via one or more transmission lines tethered to the computer device 102. As such, data receiving 302 may comprise one or more antennas, receivers, or transceivers, and may include memory for storing the received control signals.

Additionally, body part device 128 may be physically situated adjacent to one or more target body parts to allow direct or indirect electrical or magnetic or physical stimulation of one or more neurological triggers (e.g. nerves, nerve endings, receptors, etc.) associated with the body part (e.g. a muscle, tendon, or other tissue capable of moving one or more body parts, such as a finger, arm, joint, bone, leg, toe, foot, mouth, facial muscle, shoulder, or any other body part). In some examples, body part device 128 may be attached to the user via one or more attachment means (e.g. straps, bands, clips, or other means known in the art). Alternatively, the body part device 128 may be unattached to the user and stimulation signals may be transmitted to the user via one or more remote means, which may include without limitation magnetic or electronic signaling means.

Furthermore, to allow such stimulation and generate the signals or physical movement necessary for such stimulation, body part device 128 may include a body part stimulation manager 304, which may be configured to read and process the received control signals and generate one or more stimulation signals based on these received control signals. In an aspect, body part stimulation manager 304 may include a stimulation signal generating component 306, which may be configured to generate the one or more stimulation signals to be delivered to the one or more target body parts for stimulation and related movement of one or more parts of the user's body. This stimulation signal generating component 306 may generate such signal based on the one or more received control signals and may include, for example, a lookup table or other means to correlate such received control signals to the stimulation signals necessary for target body part stimulation. In addition, stimulation signal generating component 306 may include a target body part stimulating component 308, which may be configured to deliver the stimulation signal to the one or more target body parts. In an aspect, target body part stimulating component 308 may include one or more electrical leads for direct (or indirect) stimulation of the one or more target body parts, for example, by introducing one or more electrical stimulation signals to the body part or the surrounding region through the user's skin or other bodily tissue, such as bones, muscle, fatty tissue, or the like.

Figure 4:
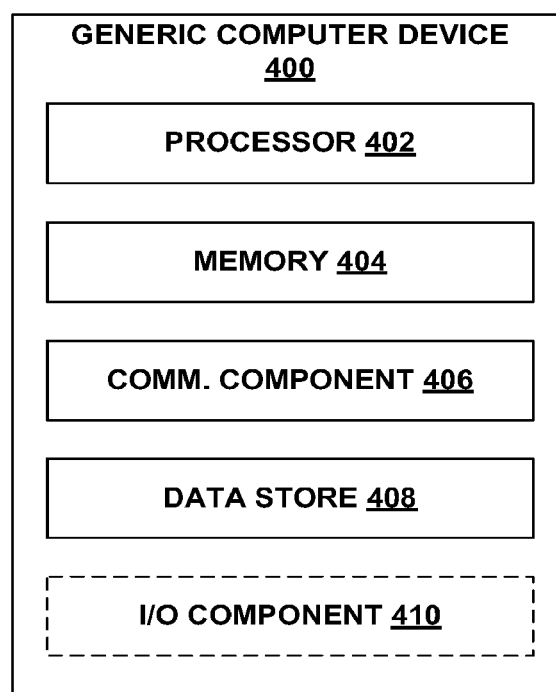
FIG. 4 is a component block diagram of aspects of a generic computer device according to aspects of the present disclosure.

Referring to FIG. 4, in one aspect, generic computer device 400 may include a specially programmed or configured computer device, and may represent or contain components that may be included in computer device 102 FIGS. 1 and 2) or body part device (FIGS. 1 and 3). Generic computer device 400 includes a processor 402 for carrying out processing processes associated with one or more components and processes described herein. Processor 402 can include a single or multiple set of processors or multi-core processors. Moreover, processor 402 can be implemented as an integrated processing system and/or a distributed processing system. Additionally, processor 402 may be configured to perform the processes described herein related to UCI behavior and/or pre-movement and action training on the generic computer device 400.

Generic computer device 400 further includes a memory 404, such as for storing data used herein and/or local versions of applications being executed by processor 402. Memory 404 can include any type of memory usable by a computer, such as random access memory (RAM), read only memory (ROM), tapes, magnetic discs, optical discs, volatile memory, non-volatile memory, and any combination thereof. Additionally, memory 404 may be configured to store data and/or code or computer-readable instructions for performing the processes described herein related to creating, controlling, manipulating, and/or instantiating a UCL Further, generic computer device 400 includes a communications component 406 that provides for establishing and maintaining communications with one or more entities utilizing one or more of hardware, software, and services as described herein. Communications component 406 may carry communication signals between components on generic computer device 400, as well as exchanging communication signals between generic computer device 400 and external devices, such as devices located across a wired or wireless communications network and/or devices serially or locally connected to generic computer device 400. For example, communications component 406 may include one or more buses, and may further include transmit chain components and receive chain components associated with a transmitter and receiver, respectively, or a transceiver, operable for interfacing with external devices.

Additionally, generic computer device 400 may further include a data store 408, which can be any suitable combination of hardware and/or software, that provides for mass storage of information, databases, and programs employed in connection with aspects described herein. For example, data store 408 may be a data repository for applications and data not currently being executed by processor 402, such as those related to the aspect described herein. In addition, generic computer device 400 may contain an input/output component 410, which may be configured to interface with one or more external devices, such as an input device (e.g. input device, user measurement device (FIG. 1)) and/or an output device (e.g. a display, feedback device, or external body part device (FIG. 1)). Specifically, input/output component 410 may contain circuitry and/or instructions that allow generic computer device 400 to connect to and/or communicate with these external devices.

Figure 5:
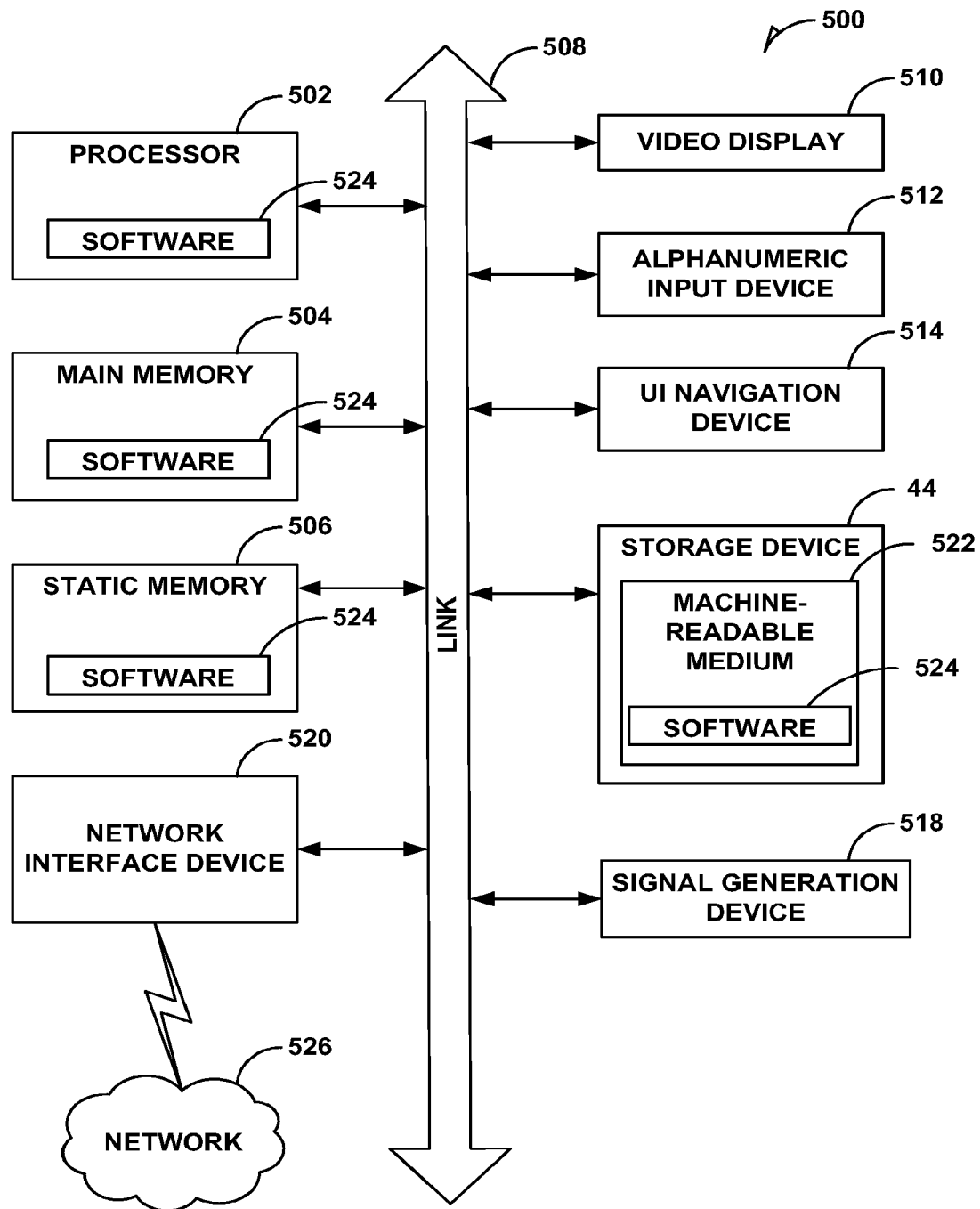
FIG. 5 is a block diagram illustrating a machine in the example form of a computer system according to an example aspect of the present disclosure.

FIG. 5 is a block diagram illustrating a machine in the example form of a computer system 500, within which a set or sequence of instructions for causing the machine to perform any one of the methodologies discussed herein may be executed, according to an example embodiment. In alternative embodiments, the machine operates as a standalone device or may be connected (e.g. networked) to other machines. In a networked deployment, the machine may operate in the capacity of either a server or a client machine in server-client network environments, or it may act as a peer machine in peer-to-peer (or distributed) network environments. The machine may be without limitation a personal computer (PC), a tablet PC, a set-top box (STB), a Personal Digital Assistant (PDA), a mobile telephone, a web appliance, a network router, switch or bridge, a cloud-based computing device, or any machine capable of executing instructions (sequential or otherwise) that specify movement and actions to be taken by that machine. Further, while only a single machine is illustrated, the term "machine" shall also be taken to include any collection of machines that individually or jointly execute a set (or multiple sets) of instructions to perform any one or more of the methodologies discussed herein.

Example computer system 500 includes at least one processor 502 (e.g. a central processing unit (CPU), a graphics processing unit (GPU) or both, processor cores, compute nodes, etc.), a main memory 504 and a static memory 505, which communicate with each other via a link 508 (e.g. bus). The computer system 500 may further include a video display unit 510, an alphanumeric input device 512 (e.g. a keyboard), and a user interface (UI) navigation device 514 (e.g. a mouse). In one embodiment, the video display unit 510, input device 512 and UI navigation device 514 are incorporated into a touch screen display. The computer system 500 may additionally include a storage device 515 (e.g. a drive unit), a signal generation device 518 (e.g. a speaker), a network interface device 520, and one or more sensors (not shown), such as a global positioning system (OPS) sensor, compass, accelerometer, or other sensor.

The storage device 515 includes a machine-readable medium 522 on which is stored one or more sets of data structures and instructions 524 (e.g. software) embodying or utilized by any one or more of the methodologies or functions described herein. The instructions 524 may also reside, completely or at least partially, within the main memory 504, static memory 505, and/or within the processor 502 during execution thereof by the computer system 500, with the main memory 504, static memory 505, and the processor 502 also constituting machine-readable media.

While the machine-readable medium 522 is illustrated in an example embodiment to be a single medium, the term "machine-readable medium" may include a single medium or multiple media (e.g. a centralized or distributed database, and/or associated caches and servers) that store the one or more instructions 524. The term "machine-readable medium" shall also be taken to include any tangible medium that is capable of storing, encoding or carrying instructions for execution by the machine and that cause the machine to perform any one or more of the methodologies of the present disclosure or that is capable of storing, encoding or carrying data structures utilized by or associated with such instructions. The term "machine-readable medium" shall accordingly be taken to include, but not be limited to, solid-state memories, and optical and magnetic media. Specific examples of machine-readable media include non-volatile memory, including, by way of example, semiconductor memory devices (e.g. Electrically Programmable Read-Only Memory (EPROM), Electrically Erasable Programmable Read-Only Memory (EEPROM)) and flash memory devices; magnetic disks such as internal hard disks and removable disks; magneto-optical disks; and CD-ROM and DVD-ROM disks.

The instructions 524 may further be transmitted or received over a communications network 526 using a transmission medium via the network interface device 520 utilizing any one of a number of well-known transfer protocols (e.g. HTTP, XML). Examples of communication networks include a local area network (LAN), a wide area network (WAN), the Internet, mobile telephone networks, Plain Old Telephone (POTS) networks, and wireless data networks (e.g. Wi-Fi, 30, and 40 LTE/LTE-A or WiMAX networks). The term "transmission medium" shall be taken to include any intangible medium that is capable of storing, encoding, or carrying instructions for execution by the machine, and includes digital or analog communications signals or other intangible medium to facilitate communication of such software.

Figure 6A:
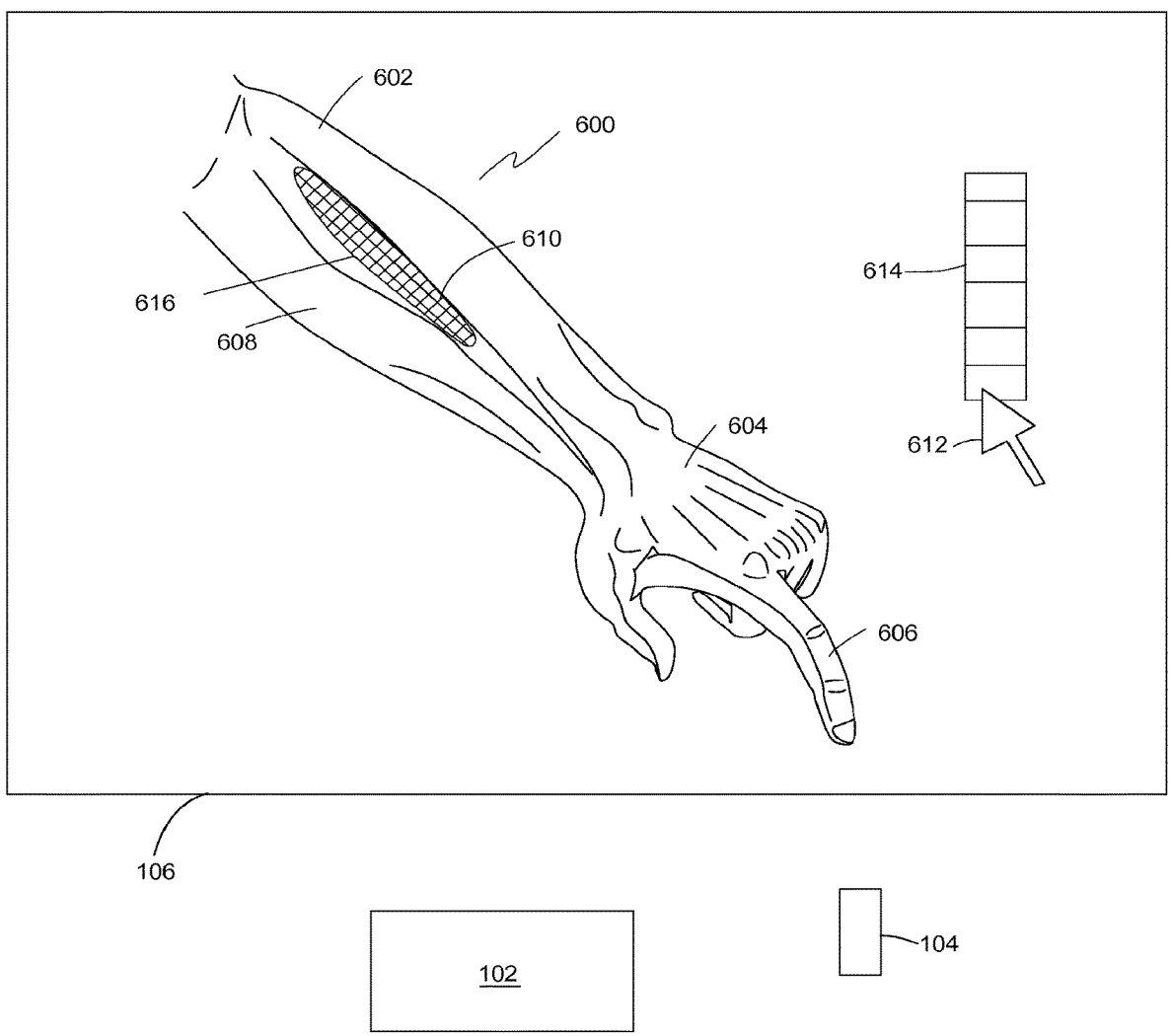
FIG. 6A illustrates a virtual body part displayed by a display device of the present invention and showing the virtual body part in a first configuration.
Figure 6B:
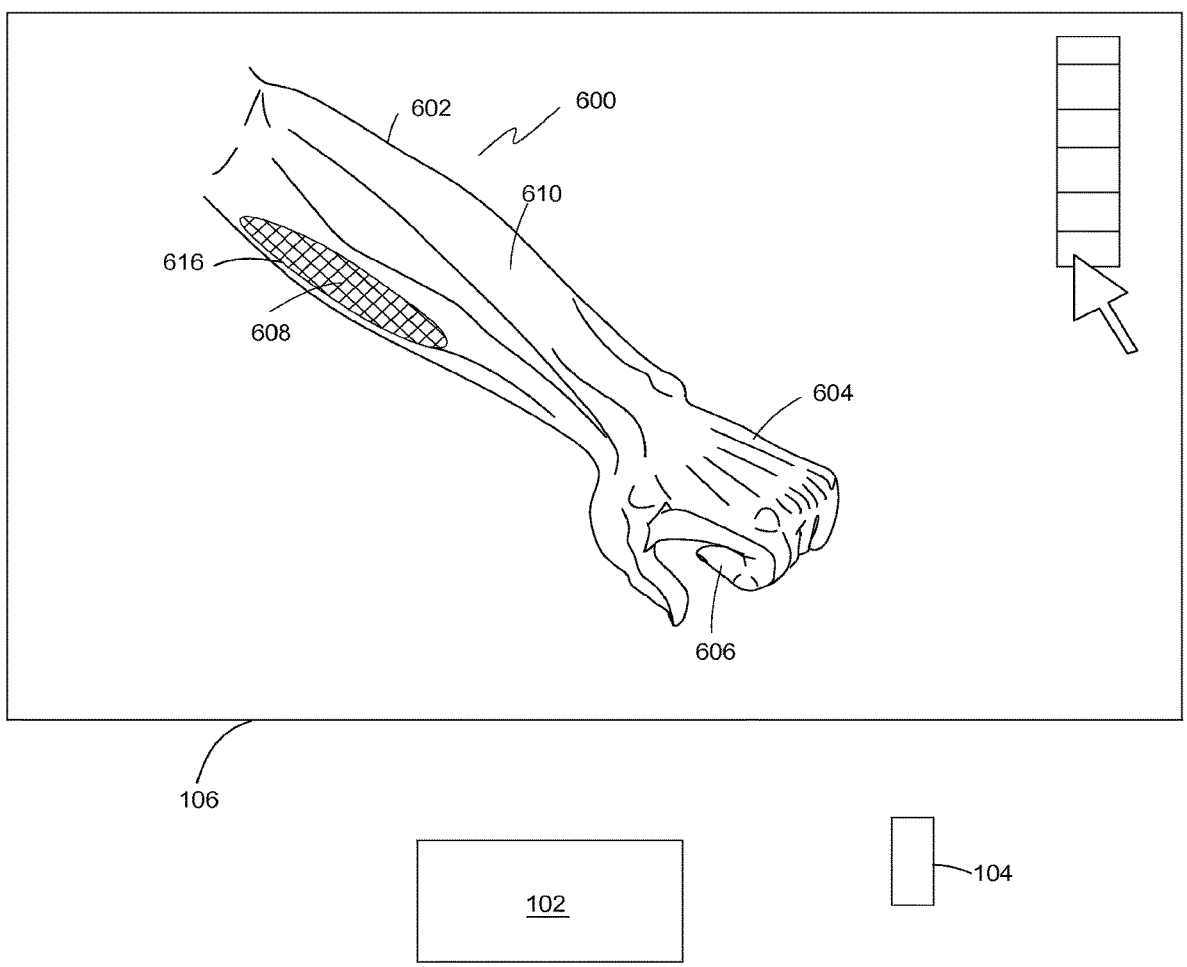
FIG. 6B illustrates the virtual body part of FIG. 6A shown in a second configuration.

Referring to FIGS. 6A and 6B in combination with FIGS. 1-2, a virtual body part 600 is shown to illustrate an example of system 100 in use with pre-movement and pre-action self-re-training/re-learning where the user seeks to self-re-learn or self-learn to perform a physical movement and action. System 100 includes computer device 102, input device 104, and display device 106. In this example, virtual body part 600 is a left forearm 602 including hand 604 and index finger 606. Selection input manager 206 of system 100 has mapped select locations associated with selection input to virtual body part 600 and parts thereof corresponding to simulated movement and actions by virtual body part 600. These select locations correspond to a user's body part that requires physical motor and related cognitive and nervous system improvements. Movement and action input manager 208 is configured to receive movement and action inputs from user 120 and system 100 generates one or more display control signals that cause virtual body part 600 to perform a movement and action.

For example, in response to user input, the user views a demonstrative movement and action of index finger 606 moving from a first configuration in which index finger 606 is extended as shown in FIG. 6A to a second configuration in which index finger 606 is flexed as shown in FIG. 6B. Index finger moves from the extended configuration to the flexed configuration by virtually stimulating a flexor muscle 608 corresponding to index finger 606. Index finger 606 moves back to the extended configuration by releasing (or ceasing to stimulate) flexor muscle 608 and stimulating an extensor muscle 610 corresponding to index finger 606. Optionally, system 100 communicates a signal to a feedback device 130, body part device 128, or target body part 150 of user 120.

In one embodiment, for example, input device 104 is a computer mouse where the user's selection is input to system 100 using the computer mouse to move a cursor 612 to a location and then clicking the mouse button to make a selection. For example, user 120 uses the computer mouse to move cursor 612 to and click on forearm 602. User 120 can click on forearm 602 generally, click on a part of forearm 602 (e.g., anterior portion), click on a particular region of forearm 602 (e.g., a particular muscle), by moving to and clicking on a list, menu 614 or indicia 616 (e.g., shaded region). Selections available to the user can be configured based on a level of detail chosen for the task to be completed, where the level of detail can be adjusted based on the user's abilities. For example, PEG level is set so that user 120 must select the particular muscle that moves index finger 606. Similarly, PEG level can be set so that user 120 must only generally select forearm 602 or near forearm 602 to have the system display the same movement and action of index finger 606.

In one embodiment, system 100 indicates the muscle or muscle group used and/or a sequence of muscle movement and actions required to perform a movement and action selected by user 120 or perform a movement and action. For example, non-stimulated muscles of virtual body part 600 (i.e., muscles at rest) are displayed in one color or intensity (e.g., brown/tan or low intensity) and muscles actively being stimulated are displayed in a second color or intensity (e.g., red or high intensity). Thus, in the virtual body part 600 shown in FIG. 6B, a virtual hand 604, forearm 602, and extensor muscle 610 are displayed in brown color on display device 106. As flexor muscle 608 is stimulated, system 100 displays flexor muscle 608 of the virtual forearm 602 in red color or using other indicia 616 in addition to displaying movement of index finger 606 from the first configuration (i.e., finger extended) to the second configuration (i.e., finger flexed) and remaining in that configuration as long as the flexor muscle 608 is stimulated. As shown in FIG. 6B, a stimulated flexor muscle 608 is accentuated on display device 106 by using indicia 616 while index finger 606 is maintained in the flexed configuration.

Figure 7:
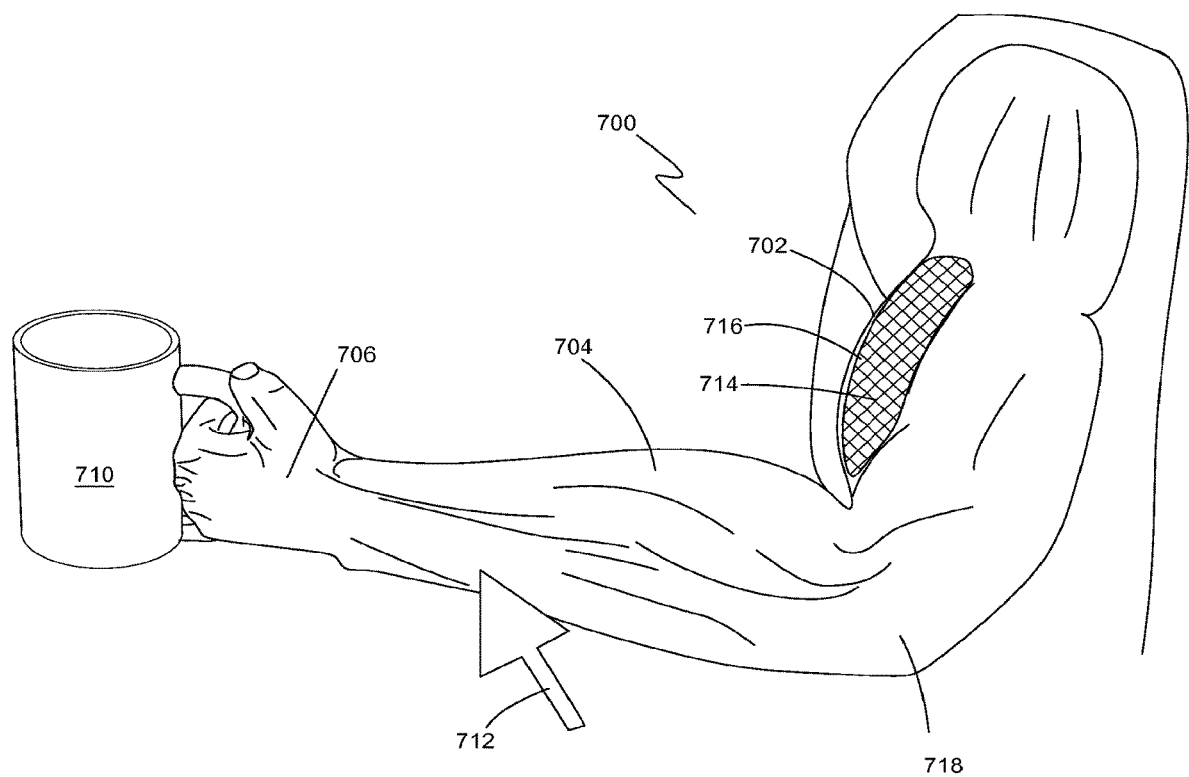
FIG. 7 illustrates an example of a virtual body part of the present invention performing the task of grasping a coffee mug.

Referring to FIG. 7, a perspective view shows another example of virtual body part 700 performing a task of grasping and moving a virtual coffee mug 710. Virtual body part 700 includes upper arm 702, forearm 704, and hand 706. User 120 selects and moves virtual body part 700 as indicated by cursor 712. In this example, user 120 may raise or lower forearm 704 by clicking on bicep muscle 714, which is emphasized on display device 106 by indicia 716 shown in FIG. 7 as cross-hatching. Using a computer mouse (not shown) as input device 104, for example, user 120 alternately may raise or lower forearm 704 by clicking cursor 712 on forearm 704 and dragging the computer mouse linearly to cause forearm 704 to pivot upwards or downwards about elbow 718. Thus, the movement and action of user 120 is non-corresponding to the displayed movement and action of virtual body part 700 since the actual linear movement of a computer mouse on a table or other surface does not correspond to the simulated pivoting movement and action of forearm 704 and also does not correspond to the same amount of simulated movement as displayed. In this example, user 120 selects hand 706 to open or close a grasp on coffee mug 710. User 120 also may orient and align virtual body part 700 in 3D virtual space by changing the displayed view of virtual body part 700 and using input device 104 to cause movements needed to relocate, pick up/set down, grasp/release, rotate, or otherwise move coffee mug 710.

Figure 8:
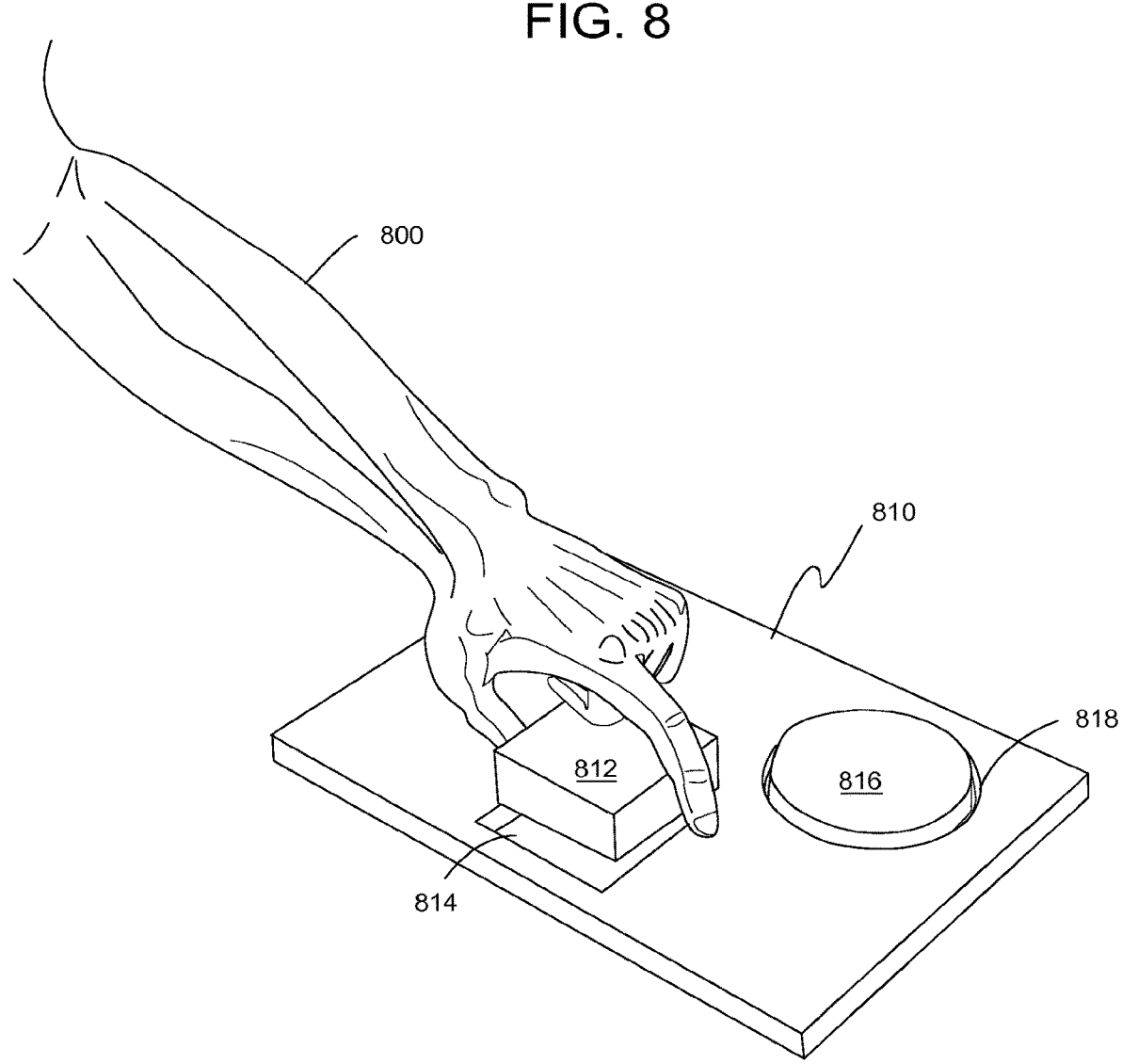
FIG. 8 illustrates an example of a pre-movement and action exercise game of the present invention in which the user uses a virtual body part to select and move blocks.

Referring now to FIG. 8, an example of a pre-movement and pre-action exercise game is illustrated as displayed to the user using display device 106 (not shown). The user is instructed to use virtual body part 800 to select and move parts of a virtual block game 810. The user controls virtual body part 800 to select blocks 812, 816 and place them into corresponding recesses 814, 818, respectively. Virtual game 800 is an example of the user being instructed to apply a rule (e.g., matching the block shape 812 with a shape of recess 814) and a condition to be met (e.g., placing block 814 into recess 814).

Referring now to FIG. 9, a flowchart illustrates steps in one embodiment of a method 900 of pre-movement and action self-training/self-learning. Method 900 is discussed with additional reference to FIGS. 1-5 above. In step 905, system 100 is provided to a user. In one embodiment, system 100 includes a computer device 102, a display device 106 disposed in communication with computer device 102, and input device 104 disposed in communication with computer device 102 as discussed above. In another embodiment, system 100 also includes feedback device 130 and/or body part device 128 disposed in communication with the computer device 102. In another embodiment, system 100 optionally includes feedback device 130.

In step 910, system 100 displays to a user a virtual body part. In one embodiment, the virtual body part is selectable or includes at least one selectable body part portion shown on display device 106 in a first position or configuration.

In step 915, system 100 optionally provides an instruction to the user to perform a task related to the virtual body part. In some embodiments, the instruction is self-evident, is provided in an instruction manual, is provided verbally by a therapist or other person, or is provided in some other form. In one embodiment, the task includes moving the virtual body part in virtual 3D space, changing the position of the virtual body part or the at least one selectable body part portion to a second position in virtual 3D space, changing the configuration of the virtual body part, moving an object in virtual 3D space, grasping a virtual object, touching a virtual object, aligning the virtual body part with a virtual object or displayed reference point, positioning the virtual body part relative to a virtual reference point such as a displayed target, using the virtual body part to select a virtual object, releasing an object, rotating at least a portion of the virtual body part in virtual 3D space, or selecting one object among a plurality of displayed objects. In one embodiment, the task includes the user identifying a condition to be met and/or application of a rule, where the user input includes or demonstrates application of the rule or identifying the condition to be met.

In step 920, system 100 receives one or more user inputs from the user. The user input can include a selection input in response to the instruction. In one embodiment, the instruction input is associated with the virtual body part or with one or more portions of the virtual body part. Alternately or additionally, the user input is a movement and action input associated with one or more portions of the virtual body part or with the entire virtual body part. In one embodiment, step 920 includes detecting a biomarker of the user. In one embodiment, step 920 is performed by input device 104, which may be user movement and action recognizing component 124.

In one embodiment, user measurement device 108 obtains a user measurement or signal, such as a neurological signal of the user, measurement of a biological substance of the user, or detection of a biomarker. System 100 optionally compares the user measurement or signal to a control value.

In optional step 925, system 100 displays to the user, in response to the user input, an indicia 616 associated with one or more selectable portions of the virtual body part. As discussed above, for example, with reference to FIGS. 6A and 6B, indicia 616 includes color, shading, intensity, a marking, a symbol, or any device that communicates to the user that a selectable portion can be selected or that a selectable portion has been selected.

In step 930, system 100 displays to the user a movement and action or movement of the virtual body part (or one or more portion thereof) to a second configuration based on the user input(s). In one embodiment, the user input(s) is (are) at least a part of pre-movement and pre-action self re-training/re-learning by the user to make physical movements.

In one embodiment, method 900 includes step 935 of system 100 outputting a control signal to a tangible body part device. Here, step 905 includes providing a system having the body part device disposed in communication with computer device 102. As discussed above, examples of body part device include a prosthetic limb or body part, a robotic device, or other tangible and operable device. In one embodiment, the body part device is operationally connected to the user, such as a prosthetic limb. In another embodiment, the body part device is not connected to the user, such as a prosthetic or robotic device positioned adjacent system 100.

When system 100 includes feedback device 130, method 900 optionally includes step 940 of providing feedback to the user. In one embodiment, the feedback is an electrical signal configured to stimulate a muscle or nerve of the user (e.g., a neurological signal), tactile feedback (e.g., via a haptic device), visual feedback, demonstrative feedback (e.g., demonstrated movement and action using a virtual body part or a tangible body part device), audio feedback, or an electrical signal configured to control a tangible body part device disposed in communication with system 100. When the feedback is an electrical signal configured to control a tangible body part device, the body part device preferably is connected to the user. In one embodiment, the electrical signal contemporaneously causes the tangible body part device to substantially perform the movement and action performed by the virtual body part.

In one embodiment, method 900 optionally includes steps 945-955. In step 945, system 100 displays a demonstrative movement and action of the virtual body part. For example, system 100 shows a virtual body part moving a hand from an open position to a closed position.

In step 950, system 100 indicates to the user one or more portion of the virtual body part that is used to perform the demonstrative movement and action. For example, system 100 displays in a different color the muscle(s) or muscle group(s) used by the virtual body part to open and close the hand. In step 950, system instructing the user to mimic the demonstrative movement and action. The instruction may be presented to the user by an on-screen message, audible command, or other means of communication.

In step 955, in response to instructing the user to mimic the demonstrative movement and action, system 100 receives a user input corresponding to the portion(s) of the virtual body part used to perform the demonstrative movement and action. For example, the user selects the muscle group used to close the hand. In response to the user input, system 100 displays the demonstrative movement and action.

Examples, as described herein, may include, or may operate on, logic or a number of modules or mechanisms. Modules are tangible entities capable of performing specified operations and may be configured or arranged in a certain manner. In an example, circuits may be arranged (e.g. internally or with respect to external entities such as other circuits) in a specified manner as a module. In an example, the whole or part of one or more computer systems (e.g. a standalone, client or server computer system) or one or more hardware processors may be configured by firmware or software (e.g. instructions, an application portion, or an application) as a module that operates to perform specified operations. In an example, the software may reside (1) on a non-transitory machine-readable medium or (2) in a transmission signal. In an example, the software, when executed by the underlying hardware of the module, causes the hardware to perform the specified operations.

Accordingly, the term "module" is understood to encompass a tangible entity, be that an entity that is physically constructed, specifically configured (e.g. hardwired), or temporarily (e.g. transitorily) configured (e.g. programmed) to operate in a specified manner or to perform part or all of any operation described herein. Considering examples in which modules are temporarily configured, one instantiation of a module may not exist simultaneously with another instantiation of the same or different module. For example, where the modules comprise a general-purpose hardware processor configured using software, the general-purpose hardware processor may be configured as respective different modules at different times. Accordingly, software may configure a hardware processor, for example, to constitute a particular module at one instance of time and to constitute a different module at a different instance of time.

Additional examples of the presently described method, system, and device embodiments include the following, non-limiting configurations. Each of the following non-limiting examples may stand on its own, or may be combined in any permutation or combination with any one or more of the other examples provided below or throughout the present disclosure. The preceding description and the drawings sufficiently illustrate specific embodiments to enable those skilled in the art to practice them. Other embodiments may incorporate structural, logical, electrical, process, and other changes. Portions and features of some embodiments may be included in, or substituted for, those of other embodiments.

As used in this disclosure, the terms "component," "module," "system" and the like are intended to include a computer-related entity, such as but not limited to hardware, firmware, a combination of hardware and software, software, or software in execution. For example, a component may be, but is not limited to being, a process running on a processor, a processor, an object, an executable, a thread of execution, a program, and/or a computer. By way of illustration, both an application running on a computing device and the computing device can be a component. One or more components can reside within a process and/or thread of execution and a component may be localized on one computer and/or distributed between two or more computers. In addition, these components can execute from various computer readable media having various data structures stored thereon. The components may communicate by way of local and/or remote processes such as in accordance with a signal having one or more data packets, such as data from one component interacting with another component in a local system, distributed system, and/or across a network such as the Internet with other systems by way of the signal.

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances; X employs A; X employs B; or X employs both A and B. In addition, the articles "a" and "an" as used in this disclosure and the appended claims should generally be construed to mean "one or more" unless specified otherwise or clear from the context to be directed to a singular form.

Various aspects or features will be presented in terms of systems that may include a number of devices, components, modules, and the like. It is to be understood and appreciated that the various systems may include additional devices, components, modules, etc. and/or may not include all of the devices, components, modules etc. discussed in connection with the figures. A combination of these approaches may also be used.

The various illustrative logics, logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the processes described herein. A general-purpose processor may be a microprocessor, but, in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Additionally, at least one processor may comprise one or more modules operable to perform one or more of the steps and/or movement and actions described above.

Further, the steps and/or movement and actions of a method or algorithm described in connection with the aspects disclosed herein may be embodied directly in hardware, in a software module executed by a processor, or in a combination of the two. A software module may reside in RAM memory, flash memory, ROM memory, EPROM memory, EEPROM memory, registers, a hard disk, a removable disk, a CD-ROM, or any other form of storage medium known in the art. An exemplary storage medium may be coupled to the processor, such that the processor can read information from, and write information to, the storage medium. In the alternative, the storage medium may be integral to the processor. Further, in some aspects, the processor and the storage medium may reside in an ASIC. Additionally, the ASIC may reside in a user terminal. In the alternative, the processor and the storage medium may reside as discrete components in a user terminal. Additionally, in some aspects, the steps and/or movement and actions of a method or algorithm may reside as one or any combination or set of codes and/or instructions on a machine readable medium and/or computer readable medium, which may be incorporated into a computer program product.

In one or more aspects, the processes described may be implemented in hardware, software, firmware, or any combination thereof. If implemented in software, the processes may be stored or transmitted as one or more instructions or code on a computer-readable medium. Computer-readable media includes both computer storage media and communication media including any medium that facilitates transfer of a computer program from one place to another. A storage medium may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Also, any connection may be termed a computer-readable medium. For example, if software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs usually reproduce data optically with lasers. Combinations of the above should also be included within the scope of computer-readable media.

Examples

Twelve survivors of acquired brain injury ("ABI") volunteered for participation in a study using PEGs alone for improving physical motor control of affected human extremities and related cognitive and nervous system processes. Each survivor was over 21 years of age. Each survivor was in chronic stages of neurological disability. Their average age was 53.9 years. The chronic conditions of survivors averaged 11.4 years from the date of injury or ABI event.

PEGs used in the study were interactive exercises displayed on a display device in which a participant, i.e. an ABI survivor-player, instantiates personal abstract mental representations (visualizations) of physical movement and actions. The survivor-player controls a virtual body part (e.g., a virtual extremity) to instantiate visual displays of simulated physical movements and actions. The visual displays used in the study were augmented by audio feedback and haptic feedback was used later in a demonstration by survivor-players. The audio feedback comprised a complimentary or encouraging sound or message to the survivor-player. The haptic feedback was provided by a haptic (vibration generating) computer mouse.

PEGs used by survivor-players includes anatomically realistic virtual extremities (limbs), with analogous true range of motion. The virtual extremities correspond to neurologically disabled extremities of the survivor-player. Virtual extremities were controlled by the survivor-player's uninvolved limb and an input device, such as, for example, a standard computer mouse, a touchscreen, or head movement tracking. For example, a PEGs survivor-player controlled any or all parts of virtual fingers, hands, lower or upper arms (right or left). The survivor-player also executed flexion/extension, supination/pronation, and abduction/adduction in any direction. The survivor-player instantiated visual displays of a portion, a majority, or all virtual upper limb movements from effectively any angle.

PEGs for virtual hand and virtual objects include (1) thumb and forefinger pincer movement and action to grasp a key; (2) two finger movement and action to grasp a ball and drop it into a cup; (3) multi-finger movement and action to pick up a spoon and drop it into a cup; (4) full hand grasp around a mug handle (see FIG. 7); (5) tapping movement and actions by index and middle fingers on a remote controller; and (6) hand grasp of objects shaped as stars, circles, or squares for placement into corresponding slots (see FIG. 8).

The virtual movement and actions were embedded into PEGs simulating real-life tasks, such as (1) opening a designated correct box, (2) selecting one box out of nine numbered boxes (with voice instructions to the survivor-player), (3) screwing and unscrewing a light bulb, (4) fitting pieces into a jigsaw puzzle, (5) selecting numbers and executing arithmetic functions, and (6) selecting letters to spell words.

Two baseline measurements (baseline 1 and baseline 2) were made two weeks apart, before any PEGs intervention. The two baseline measurements were two of the measures and the intervention outcomes was the third measure. The three-level repeated measures design was used to verify intervention outcomes as compared to baseline conditions. Each of the twelve participants averaged about 20 hours of PEGs play.

The chronic conditions of the participants were unchanged during the two week baseline period but variably improved after PEGs intervention. All results discussed below are post-intervention results.

Measurements of motor skills improvements were made by manual muscle testing using a goniometer to assess range of motion (ROM); using a calibrated dynamometer to measure hand grip strength; and using a pinch meter for testing strength for key, lateral, and three-jaw chuck (tripod) grasps. Measurements of cognitive performance were made using the Executive Function Performance Test.

Results

Shoulder Flexion:

Shoulder flexion range of motion and strength were evaluated for nine participants, those having active shoulder movement. The normal range of motion for forward shoulder flexion is about 180°. For these participants, the mean ranges of motion across the three phases of shoulder movement, adduction, abduction and supination were 99.9°, 104.3°, and 126.3°, respectively. The nonparametric Friedman test for repeated measures ANOVA showed these differences to be statistically significant (p=0.02).

Participants no. 3 and no. 6 showed marked improvements ranging from trace to fair strength, while participants no. 8 and no. 11 showed improvements from fair to normal strength.

Wrist Flexion:

Wrist flexion range of movement and wrist strength was evaluated for the participants. The normal range of movement for wrist flexion is from about 60° to about 80°. Improvements were recorded in five participants, nos. 3, 6, 7, 10, and 11. For these five participants, the range of movement improved from an average of 54° to an average of 67°. The difference was significant, as indicated by a nonparametric t-test (p=0.04).

Wrist strength remained generally stable for the participants, except for participant nos. 3, 6, and 8. These participants showed improvements in wrist strength from trace to poor, trace to fair, and good to normal, respectively.

Elbow Flexion:

Elbow flexion range of movement and elbow strength were evaluated for the participants. The normal range of motion for elbow flexion is about 150°. Slight improvements were observed in participant no. 4 (5°), no. 11 (13°), and no. 12 (5°). The mean range of motion for these three participants increased slightly from 120.2°, 121.0°, and 131.5°, respectively.

Participants no. 3, no. 6, and no. 8 showed improvements in elbow strength from trace to poor, trace to fair, and good to normal, respectively.

Cognitive Skills:

Cognitive skills of the participants were evaluated using the Executive Function Performance Test ("EFPT"). The EFPT measured participants' skills in initiation, organization, sequencing and safety. The EFPT tasks were cooking, taking medication, placing telephone calls, and paying bills. Activity demands of the EFPT included opening medicine bottles, reaching and using cooking tools, and using a calculator for paying bills.

For overall EFPT task completion, ten participants performed at the level of complete independence following PEG intervention. The mean difference in cognitive skills from baseline 2 to intervention was statistically significant (p=0.02).

Nine participants demonstrated improvement in overall task performance. Improvement was noticeable in seven participants (nos. 1, 2, 3, 4, 6, 7, and 8). The mean difference on the global EFPT score from baseline 2 to intervention was statistically significant (p=0.02).

While the foregoing disclosure discusses illustrative aspects and/or embodiments, it should be noted that various changes and modifications could be made herein without departing from the scope of the described aspects and/or embodiments as defined by the appended claims. Furthermore, although elements of the described aspects and/or embodiments may be described or claimed in the singular, the plural is contemplated unless limitation to the singular is explicitly stated. Additionally, all or a portion of any aspect and/or embodiment may be utilized with all or a portion of any other aspect and/or embodiment, unless stated otherwise.

We claim:

1. A system for improvement of a user's movement control of a body part and related cognitive and nervous system processes comprising:
   a computer device;
   a tangible body part device disposed in communication with the computer device;
   a display device in communication with the computer device;
   an input device in communication with the computer device;
   the computer device having a processing engine including an execution component, and a memory device that stores instructions which, when executed, configure the computer device to:
   execute, via the execution component, a movement and action exercise;
   display to a user, via the display device, a virtual body part image in a first configuration on the display device, wherein the virtual body part image corresponds to the user's corresponding body part requiring improvement of movement control;
   prompt the user, via a selection manager, to provide at least one selection input signal via the input device; wherein the selection input signal corresponds to a user selected area of the virtual body part image;
   receive, at the selection manager, the selection input signal via the input device used by the user;
   map, by the selection manager, the selection input signal to the virtual body part image; wherein the selection manager causes a virtual body part manager to indicate, on the displayed virtual body part image, the area of the virtual body part image selected by the user;
   prompt the user, via a movement and action manager, to provide at least one movement and action input signal via the input device;
   receive, at the movement and action manager, the movement and action input signal from the input device being used by the user, wherein the movement and action input signal corresponds to a movement of the user;
   storing, via a user-configured user-controllable image manager, a user characteristic data, wherein the user characteristic data includes data associated with user performance;
   generate, via the movement and action manager, a display control signal that directs a displaying of the virtual body part image area selected by the user moving from the first configuration on the display device to a second configuration on the display device in accordance with the received movement and action input signal and in accordance with user characteristic data;
   generate, via a body part interface component, a control signal to the tangible body part device to contemporaneously cause the tangible body part device to substantially perform the same movements as the user directed displaying of the movement and action of the virtual body part image; and wherein the displayed virtual body part image movement from the first configuration on the display device to a second configuration on the display device does not correspond to the movement of the user.

2. The system of claim 1, wherein the computer device is further configured to provide to the user an instruction to perform one or more tasks selected from a group comprising: moving the virtual body part image in virtual 3D space, changing the first configuration of the virtual body part image to a second configuration of the virtual body part image in virtual 3D space, moving a virtual object in virtual 3D space, grasping a virtual object, touching a virtual object, aligning the virtual body part image with a virtual object, positioning the virtual body part image relative to a virtual reference point, orientating the virtual body part image relative to a virtual reference point, using the virtual body part image to select a virtual object, moving the virtual body part image, releasing the virtual body part image, and rotating at least a portion of the virtual body part image in virtual 3D space.

3. The system of claim 1, wherein the computer device is further configured to provide to the user an instruction to perform a task selected from the group comprising: aligning the virtual body part image with a displayed reference point, guiding the virtual body part image to select one object among a plurality of displayed objects, and moving the virtual body part image to a displayed target.

4. The system of claim 1, further comprising:
a user measurement device configured to detect a biomarker of the user;
wherein the computer device is configured to correlate, via the movement and action manager, the biomarker to the movement and action input signal.

5. The system of claim 1, further comprising:
a user measurement device configured to detect a neurological signal of the user;
wherein the computer device is configured to correlate, via the movement and action manager, the neurological signal to the movement and action input signal.

6. The system of claim 1, wherein the computer device is configured to display an indicia on the displayed virtual body part image to indicate the area of the virtual body part image selected by the user.

7. The system of claim 1, further comprising a feedback device disposed in communication with the computer device, wherein the feedback device provides feedback to the user, wherein the feedback is selected from the group comprising: a visual feedback and an audio feedback.

8. The system of claim 1 further comprising the tangible body part device is disposed in communication with the computer device, and wherein the tangible body part device provides feedback to the user selected from the group comprising: a signal stimulating the skin of the user, a signal stimulating the nerves of the user, a signal stimulating the muscles of the user, and a tactile feedback.

9. The system of claim 8, wherein the tangible body part device is physically attached to the user.

10. The system of claim 1, further comprising:
a user measurement device configured to obtain at least one user measurement and to compare the user measurement to a control value, wherein the user measurement is selected from the group comprising: a neurological signal measurement, a biological substance measurement, and a biomarker measurement; and
the memory device further stores instructions which, when executed, configure the computer device to store obtained user measurement in the memory device.

11. The system of claim 1, wherein the computer device is further configured to
(i) display a demonstrative virtual movement of the virtual body part image;
(ii) indicate to the user at least one portion of the virtual body part image used to perform the demonstrative virtual movement;
(iii) instruct the user to mimic the demonstrative virtual movement by entering selection input signals;
(iv) receive the selection input signals, wherein each of the selection input signals perform one of a selection or a de-selection associated with the user selected area of the virtual body part image used to perform the demonstrative virtual movement;
(v) instruct the user to mimic the demonstrative virtual movement and action by providing movement and action input signals; and
(vi) receive the movement and action input signals, wherein each of the movement and action input signals is associated with the at least one portion of the virtual body part image used to perform the demonstrative virtual movement.

12. The system of claim 1, wherein the movement and action manager is configured to tailor movement and action training activities based upon stored user characteristic data.

* * * * *